United States Patent
Rowe et al.

(10) Patent No.: US 12,115,065 B2
(45) Date of Patent: Oct. 15, 2024

(54) PROSTHETIC HEART VALVE ASSEMBLY

(71) Applicant: EDWARDS LIFESCIENCES CORPORATION, Irvine, CA (US)

(72) Inventors: Stanton J. Rowe, Newport Coast, CA (US); Mark Chau, Laguna Hills, CA (US); Son V. Nguyen, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/209,213

(22) Filed: Jun. 13, 2023

(65) Prior Publication Data

US 2023/0320847 A1    Oct. 12, 2023

Related U.S. Application Data

(63) Continuation of application No. 17/203,611, filed on Mar. 16, 2021, now Pat. No. 11,717,401, which is a (Continued)

(51) Int. Cl.
*A61F 2/24* (2006.01)
*A61F 2/90* (2013.01)
(Continued)

(52) U.S. Cl.
CPC .......... *A61F 2/2418* (2013.01); *A61F 2/2427* (2013.01); *A61F 2/2436* (2013.01);
(Continued)

(58) Field of Classification Search
CPC ........ A61F 2/24; A61F 2/2409; A61F 2/2412; A61F 2/2454; A61F 2/2457; A61F 2/246;
(Continued)

(56) References Cited

U.S. PATENT DOCUMENTS

| 3,409,013 A | 11/1968 | Berry |
| 3,472,230 A | 10/1969 | Fogarty |

(Continued)

FOREIGN PATENT DOCUMENTS

| DE | 2246526 A1 | 3/1973 |
| DE | 19532846 A1 | 3/1997 |

(Continued)

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

(Continued)

*Primary Examiner* — Seema Mathew
(74) *Attorney, Agent, or Firm* — Thomas C. Richardson

(57) ABSTRACT

A prosthetic heart valve assembly includes a self-expandable stent having a flared upper portion, a lower portion, and an intermediate portion extending from the upper portion to the lower portion. The stent includes upwardly bent hooks extending from an outer surface of the stent, which are adapted to engage native leaflet tissue. The stent further includes an elongate anchoring member extending from the lower portion of the stent, which is adapted to be secured to a ventricle wall via a prong portion. When deployed within the native heart valve, the flared upper portion contacts a supra-annular surface of the native heart valve for preventing downward migration of the prosthetic heart valve assembly toward the ventricle and the upwardly bent hooks and the elongate anchoring member prevent upward migration of the prosthetic heart valve assembly toward an atrium.

21 Claims, 16 Drawing Sheets

Related U.S. Application Data continuation of application No. 16/238,344, filed on Jan. 2, 2019, now Pat. No. 10,952,846, which is a continuation of application No. 15/683,611, filed on Aug. 22, 2017, now Pat. No. 10,617,520, which is a continuation of application No. 14/584,903, filed on Dec. 29, 2014, now Pat. No. 10,226,334, which is a continuation of application No. 13/660,875, filed on Oct. 25, 2012, now abandoned, which is a continuation of application No. 12/113,418, filed on May 1, 2008, now abandoned.

(51) Int. Cl.
*A61L 27/36* (2006.01)
*A61L 27/50* (2006.01)
*A61B 17/00* (2006.01)
*A61B 17/04* (2006.01)

(52) U.S. Cl.
CPC .............. *A61F 2/2454* (2013.01); *A61F 2/90* (2013.01); *A61L 27/3625* (2013.01); *A61L 27/50* (2013.01); *A61B 2017/00243* (2013.01); *A61B 17/0401* (2013.01); *A61B 2017/0417* (2013.01); *A61B 2017/0496* (2013.01); *A61F 2/2457* (2013.01); *A61F 2210/0014* (2013.01); *A61F 2220/0008* (2013.01); *A61F 2220/0016* (2013.01); *A61F 2230/0054* (2013.01); *A61F 2230/0067* (2013.01); *A61F 2230/0078* (2013.01); *A61F 2250/0039* (2013.01); *A61L 2430/20* (2013.01)

(58) Field of Classification Search
CPC ............ A61F 2/2418; A61F 2220/0016; A61F 2220/0008; A61F 2/2463; A61F 2002/8486; A61F 2/82; A61F 2002/8483
See application file for complete search history.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,898,701 A | 8/1975 | La Russa |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,607,465 A | 3/1997 | Camilli |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A * | 1/1999 | Bessler ................ A61F 2/2418 623/2.38 |
| 5,855,602 A | 1/1999 | Angell |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,287,334 B1 | 9/2001 | Moll et al. |

(56) References Cited

U.S. PATENT DOCUMENTS

| | | |
|---|---|---|
| 6,299,637 B1 | 10/2001 | Shaolian et al. |
| 6,302,906 B1 | 10/2001 | Goicoechea et al. |
| 6,312,464 B1 | 11/2001 | Navia |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1* | 10/2002 | Bailey .................. A61F 2/2469 623/1.26 |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,540,782 B1 | 4/2003 | Snyders |
| 6,569,196 B1 | 5/2003 | Vesely |
| 6,582,462 B1 | 6/2003 | Andersen et al. |
| 6,602,288 B1 | 8/2003 | Cosgrove et al. |
| 6,605,112 B1 | 8/2003 | Moll et al. |
| 6,709,456 B2 | 3/2004 | Langberg et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,752,813 B2 | 6/2004 | Goldfarb et al. |
| 6,764,510 B2 | 7/2004 | Vidlund et al. |
| 6,767,362 B2 | 7/2004 | Schreck |
| 6,790,231 B2 | 9/2004 | Liddicoat et al. |
| 6,797,002 B2 | 9/2004 | Spence et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,101,395 B2 | 9/2006 | Tremulis et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,404,824 B1 | 7/2008 | Webler et al. |
| 7,462,191 B2 | 12/2008 | Spenser et al. |
| 7,510,575 B2 | 3/2009 | Spenser et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,678,145 B2 | 3/2010 | Vidlund et al. |
| 7,993,394 B2 | 8/2011 | Hariton et al. |
| 8,007,992 B2 | 8/2011 | Tian et al. |
| 8,029,556 B2 | 10/2011 | Rowe |
| 8,167,932 B2 | 5/2012 | Bourang et al. |
| 8,932,348 B2* | 1/2015 | Solem .................. A61B 17/0401 623/2.11 |
| 8,968,395 B2* | 3/2015 | Hauser .................. A61F 2/2436 623/2.36 |
| 8,992,604 B2 | 3/2015 | Gross et al. |
| 9,078,749 B2 | 7/2015 | Lutter et al. |
| 9,095,433 B2 | 8/2015 | Lutter et al. |
| 9,254,192 B2 | 2/2016 | Lutter et al. |
| 9,662,203 B2* | 5/2017 | Sheahan .................. A61F 2/2418 |
| 9,986,993 B2* | 6/2018 | Vidlund .................. A61F 2/2457 |
| 10,271,949 B2* | 4/2019 | Dakin .................. A61F 2/2418 |
| 10,292,816 B2* | 5/2019 | Raanani .................. A61F 2/243 |
| 10,321,991 B2* | 6/2019 | Glimsdale .................. A61F 2/2418 |
| 10,321,992 B2* | 6/2019 | Quill .................. A61F 2/2427 |
| 10,433,953 B2* | 10/2019 | Wallace .................. A61F 2/2418 |
| 10,441,417 B2* | 10/2019 | Braido .................. A61F 2/915 |
| 10,441,421 B2* | 10/2019 | Perszyk .................. A61F 2/848 |
| 10,456,243 B2* | 10/2019 | Robertson .................. A61F 2/2418 |
| 10,500,038 B1* | 12/2019 | Orlov .................. A61F 2/2418 |
| 10,729,541 B2* | 8/2020 | Francis .................. A61F 2/2412 |
| 10,881,512 B2* | 1/2021 | Cooper .................. A61F 2/24 |
| 10,945,836 B2* | 3/2021 | Braido .................. A61F 2/2418 |
| 11,278,398 B2* | 3/2022 | Salahieh .................. A61F 2/2412 |
| 11,559,400 B2* | 1/2023 | Maisano .................. A61F 2/2454 |
| 11,602,429 B2* | 3/2023 | Fung .................. A61F 2/2436 |
| 11,684,471 B2* | 6/2023 | Cooper .................. A61F 2/2418 623/2.14 |
| 11,717,401 B2* | 8/2023 | Rowe .................. A61F 2/2436 623/2.14 |
| 11,759,318 B2* | 9/2023 | Vidlund .................. A61F 2/2418 623/1.14 |
| 11,850,147 B2* | 12/2023 | Oba .................. A61B 17/00234 |
| 11,911,270 B2* | 2/2024 | Chuter .................. A61F 2/2418 |
| 12,004,949 B2* | 6/2024 | Ratz .................. A61F 2/2418 |
| 2001/0021872 A1 | 9/2001 | Bailey et al. |
| 2002/0026216 A1 | 2/2002 | Grimes |
| 2002/0032481 A1 | 3/2002 | Gabbay |
| 2002/0128708 A1 | 9/2002 | Northrup et al. |
| 2002/0138138 A1 | 9/2002 | Yang |
| 2002/0151970 A1 | 10/2002 | Garrison et al. |
| 2002/0173842 A1 | 11/2002 | Buchanan |
| 2003/0023303 A1* | 1/2003 | Palmaz .................. A61F 2/2418 623/2.18 |
| 2003/0050694 A1 | 3/2003 | Yang et al. |
| 2003/0078465 A1 | 4/2003 | Pai et al. |
| 2003/0078654 A1 | 4/2003 | Taylor et al. |
| 2003/0100939 A1 | 5/2003 | Yodfat et al. |
| 2003/0130731 A1 | 7/2003 | Vidlund et al. |
| 2003/0153946 A1 | 8/2003 | Kimblad |
| 2003/0171776 A1 | 9/2003 | Adams et al. |
| 2003/0199975 A1 | 10/2003 | Gabbay |
| 2003/0212454 A1 | 11/2003 | Scott et al. |
| 2004/0002719 A1 | 1/2004 | Oz et al. |
| 2004/0019378 A1 | 1/2004 | Hlavka et al. |
| 2004/0024414 A1 | 2/2004 | Downing |
| 2004/0039436 A1 | 2/2004 | Spenser et al. |
| 2004/0059351 A1 | 3/2004 | Eigler et al. |
| 2004/0060563 A1 | 4/2004 | Rapacki et al. |
| 2004/0087975 A1 | 5/2004 | Lucatero et al. |
| 2004/0092858 A1 | 5/2004 | Wilson et al. |
| 2004/0106989 A1 | 6/2004 | Wilson et al. |
| 2004/0122448 A1 | 6/2004 | Levine |
| 2004/0127979 A1 | 7/2004 | Wilson et al. |
| 2004/0133263 A1 | 7/2004 | Dusbabek et al. |
| 2004/0138743 A1 | 7/2004 | Myers et al. |
| 2004/0138745 A1 | 7/2004 | Macoviak et al. |
| 2004/0167539 A1 | 8/2004 | Kuehn et al. |
| 2004/0186563 A1 | 9/2004 | Lobbi |
| 2004/0186565 A1 | 9/2004 | Schreck |
| 2004/0193259 A1 | 9/2004 | Gabbay |
| 2004/0210307 A1 | 10/2004 | Khairkhahan |
| 2004/0225354 A1 | 11/2004 | Allen et al. |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2004/0260393 A1 | 12/2004 | Rahdert et al. |
| 2005/0004668 A1 | 1/2005 | Aklog et al. |
| 2005/0010287 A1 | 1/2005 | Macoviak et al. |
| 2005/0033398 A1 | 2/2005 | Seguin |
| 2005/0038508 A1 | 2/2005 | Gabbay |
| 2005/0038509 A1 | 2/2005 | Ashe |
| 2005/0043790 A1 | 2/2005 | Seguin |
| 2005/0049692 A1 | 3/2005 | Numamoto et al. |
| 2005/0070999 A1 | 3/2005 | Spence |
| 2005/0075719 A1 | 4/2005 | Bergheim |
| 2005/0075724 A1 | 4/2005 | Svanidze et al. |
| 2005/0075725 A1 | 4/2005 | Rowe |
| 2005/0075727 A1 | 4/2005 | Wheatley |
| 2005/0124969 A1 | 6/2005 | Fitzgerald et al. |
| 2005/0137686 A1* | 6/2005 | Salahieh .................. A61F 2/2439 623/2.11 |
| 2005/0192581 A1 | 9/2005 | Molz et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288766 A1 | 12/2005 | Plain et al. |
| 2006/0020327 A1 | 1/2006 | Lashinski et al. |
| 2006/0025857 A1 | 2/2006 | Bergheim et al. |
| 2006/0052867 A1 | 3/2006 | Revuelta et al. |

(56) References Cited

U.S. PATENT DOCUMENTS

| | | |
|---|---|---|
| 2006/0074483 A1 | 4/2006 | Schrayer |
| 2006/0074484 A1 | 4/2006 | Huber |
| 2006/0149350 A1 | 7/2006 | Patel et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0229719 A1 | 10/2006 | Marquez et al. |
| 2006/0241745 A1 | 10/2006 | Solem |
| 2006/0259136 A1 | 11/2006 | Nguyen et al. |
| 2006/0259137 A1 | 11/2006 | Artof et al. |
| 2006/0276813 A1 | 12/2006 | Greenberg |
| 2006/0282161 A1 | 12/2006 | Huynh et al. |
| 2006/0287717 A1* | 12/2006 | Rowe .............. A61F 2/2445 623/2.11 |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0043435 A1 | 2/2007 | Seguin et al. |
| 2007/0093890 A1 | 4/2007 | Eliasen et al. |
| 2007/0112422 A1 | 5/2007 | Dehdashtian |
| 2007/0142906 A1 | 6/2007 | Figulla et al. |
| 2007/0203575 A1 | 8/2007 | Forster et al. |
| 2007/0213813 A1 | 9/2007 | Von Segesser et al. |
| 2007/0255389 A1 | 11/2007 | Oberti et al. |
| 2007/0270943 A1 | 11/2007 | Solem et al. |
| 2007/0282429 A1 | 12/2007 | Hauser et al. |
| 2008/0009940 A1* | 1/2008 | Cribier ............ A61F 2/2415 623/2.11 |
| 2008/0039935 A1 | 2/2008 | Buch et al. |
| 2008/0065011 A1 | 3/2008 | Marchand et al. |
| 2008/0071369 A1* | 3/2008 | Tuval .............. A61F 2/2436 623/2.38 |
| 2008/0086164 A1* | 4/2008 | Rowe .............. A61F 2/2466 606/191 |
| 2008/0114442 A1 | 5/2008 | Mitchell et al. |
| 2008/0154355 A1 | 6/2008 | Benichou et al. |
| 2008/0161911 A1 | 7/2008 | Revuelta et al. |
| 2008/0183273 A1 | 7/2008 | Mesana et al. |
| 2008/0243245 A1 | 10/2008 | Thambar et al. |
| 2009/0131880 A1 | 5/2009 | Speziali et al. |
| 2009/0157175 A1 | 6/2009 | Benichou |
| 2009/0164005 A1 | 6/2009 | Dove et al. |
| 2009/0171456 A1 | 7/2009 | Kveen et al. |
| 2009/0276040 A1* | 11/2009 | Rowe .............. A61F 2/90 623/2.18 |
| 2009/0281619 A1 | 11/2009 | Le et al. |
| 2009/0319037 A1 | 12/2009 | Rowe et al. |
| 2010/0036479 A1 | 2/2010 | Hill et al. |
| 2010/0049313 A1 | 2/2010 | Alon et al. |
| 2010/0204781 A1 | 8/2010 | Alkhatib |
| 2011/0004296 A1 | 1/2011 | Lutter et al. |
| 2011/0015729 A1 | 1/2011 | Jimenez et al. |
| 2011/0077733 A1 | 3/2011 | Solem |
| 2011/0313515 A1* | 12/2011 | Quadri ............ A61F 2/2418 623/2.22 |
| 2011/0319989 A1 | 12/2011 | Lane et al. |
| 2012/0022640 A1* | 1/2012 | Gross .............. A61F 2/2427 623/2.11 |
| 2012/0101571 A1 | 4/2012 | Thambar et al. |
| 2012/0123529 A1 | 5/2012 | Levi et al. |
| 2012/0179244 A1* | 7/2012 | Schankereli ...... A61F 2/2418 623/2.11 |
| 2013/0116779 A1 | 5/2013 | Weber |
| 2013/0172978 A1* | 7/2013 | Vidlund .......... A61B 17/0401 623/1.12 |
| 2013/0184811 A1* | 7/2013 | Rowe .............. A61F 2/2418 623/2.11 |
| 2013/0304200 A1 | 11/2013 | McLean et al. |
| 2013/0338763 A1* | 12/2013 | Rowe .............. A61F 2/2463 623/2.11 |
| 2014/0155997 A1* | 6/2014 | Braido ............ A61F 2/2409 623/2.37 |
| 2014/0194981 A1* | 7/2014 | Menk ............. A61F 2/2418 623/2.17 |
| 2014/0296969 A1* | 10/2014 | Tegels ............ A61F 2/2412 623/2.11 |
| 2014/0309732 A1* | 10/2014 | Solem ............ A61F 2/2412 623/2.36 |
| 2015/0066140 A1* | 3/2015 | Quadri ........... A61F 2/2436 623/2.11 |
| 2015/0127096 A1* | 5/2015 | Rowe ............. A61L 27/50 623/2.14 |
| 2015/0223934 A1* | 8/2015 | Vidlund .......... A61B 17/0401 623/2.11 |
| 2015/0342733 A1* | 12/2015 | Alkhatib ......... A61F 2/2409 623/2.17 |
| 2016/0151155 A1 | 6/2016 | Lutter et al. |
| 2016/0235529 A1* | 8/2016 | Ma .............. A61F 2/2418 |
| 2016/0354201 A1* | 12/2016 | Keogh ........... A61F 2/2418 |
| 2017/0095333 A1* | 4/2017 | Rowe ............ A61F 2/2418 |
| 2017/0172737 A1* | 6/2017 | Kuetting ......... A61F 2/2418 |
| 2017/0216027 A1* | 8/2017 | Marchand ....... A61F 2/2436 |
| 2017/0312077 A1* | 11/2017 | Vidlund ......... A61F 2/2439 |
| 2017/0312078 A1* | 11/2017 | Krivoruchko .... A61F 2/2418 |
| 2017/0348098 A1* | 12/2017 | Rowe ............ A61F 2/2427 |
| 2018/0078370 A1* | 3/2018 | Kovalsky ........ A61F 2/2433 |
| 2018/0289473 A1* | 10/2018 | Rajagopal ....... A61F 2/2418 |
| 2018/0289474 A1* | 10/2018 | Rajagopal ....... A61F 2/2418 |
| 2018/0318083 A1* | 11/2018 | Bolling .......... A61B 17/0401 |
| 2019/0015205 A1* | 1/2019 | Rajagopal ....... A61B 17/0401 |
| 2019/0060070 A1* | 2/2019 | Groothuis ....... A61F 2/2466 |
| 2019/0175339 A1* | 6/2019 | Vidlund ......... A61F 2/2418 |
| 2020/0078000 A1* | 3/2020 | Rajagopal ....... A61F 2/2409 |
| 2020/0155307 A1* | 5/2020 | Quijano ......... A61F 2/2436 |
| 2021/0000596 A1* | 1/2021 | Rajagopal ....... A61F 2/2418 |
| 2021/0030537 A1* | 2/2021 | Tegels ........... A61F 2/2409 |
| 2021/0077083 A1* | 3/2021 | Thambar ........ A61F 2/2418 |
| 2021/0196457 A1* | 7/2021 | Rowe ............ A61F 2/2454 |
| 2021/0346153 A1* | 11/2021 | Vietmeier ....... A61F 2/2436 |
| 2021/0386542 A1* | 12/2021 | Schankereli ..... A61F 2/2436 |
| 2022/0008201 A1* | 1/2022 | Passman ........ A61F 2/246 |
| 2022/0031452 A1* | 2/2022 | Alleleyn ........ A61F 2/2418 |
| 2022/0087814 A1* | 3/2022 | Vidlund ......... A61F 2/2436 |
| 2022/0110747 A1* | 4/2022 | Morriss ......... A61F 2/2418 |
| 2022/0240922 A1* | 8/2022 | Rajagopal ....... A61F 2/2412 |
| 2022/0346948 A1* | 11/2022 | Morriss ......... A61F 2/2418 |
| 2023/0079014 A1* | 3/2023 | Hayes ........... A61F 2/2412 623/2.1 |
| 2023/0277304 A1* | 9/2023 | Von Oepen ..... A61F 2/2418 623/2.38 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| DE | 102007043830 A1 | 4/2009 |
| DE | 102007043831 A1 | 4/2009 |
| EP | 0103546 A1 | 3/1984 |
| EP | 0144167 A2 | 6/1985 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1472996 A1 | 11/2004 |
| EP | 1570809 A1 | 9/2005 |
| FR | 2728457 A1 | 6/1996 |
| FR | 2788217 A1 | 7/2000 |
| GB | 2056023 A | 3/1981 |
| SE | 531468 C2 | 4/2009 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930647 A1 | 6/1999 |

(56) References Cited

FOREIGN PATENT DOCUMENTS

| | | |
|---|---|---|
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0044311 A2 | 8/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 02062236 A1 | 8/2002 |
| WO | 03003943 A2 | 1/2003 |
| WO | 03003949 A2 | 1/2003 |
| WO | 03028558 A2 | 4/2003 |
| WO | 03030776 A2 | 4/2003 |
| WO | 03047468 A1 | 6/2003 |
| WO | 03055417 A1 | 7/2003 |
| WO | 03094795 A1 | 11/2003 |
| WO | 03094796 A1 | 11/2003 |
| WO | 2004012583 A2 | 2/2004 |
| WO | 2004014258 A1 | 2/2004 |
| WO | 2004021893 A1 | 3/2004 |
| WO | 2004030568 A2 | 4/2004 |
| WO | 2004045378 A2 | 6/2004 |
| WO | 2005007036 A1 | 1/2005 |
| WO | 2005027797 A1 | 3/2005 |
| WO | 2005069850 A2 | 8/2005 |
| WO | 2005087140 A1 | 9/2005 |
| WO | 2006014233 A2 | 2/2006 |
| WO | 2006029062 A1 | 3/2006 |
| WO | 2006032051 A2 | 3/2006 |
| WO | 2006034008 A2 | 3/2006 |
| WO | 2006049629 A1 | 5/2006 |
| WO | 2006089236 A1 | 8/2006 |
| WO | 2006111391 A1 | 10/2006 |
| WO | 2006127756 A2 | 11/2006 |
| WO | 2006127765 A1 | 11/2006 |
| WO | 2007140470 A2 | 12/2007 |
| WO | 2008005405 A2 | 1/2008 |
| WO | 2008028569 A1 | 3/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009134701 A2 | 11/2009 |
| WO | 2010091653 A1 | 8/2010 |
| WO | 2010121076 A2 | 10/2010 |

OTHER PUBLICATIONS

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der Verschluß des Ductus Arteriosus Persistens ohne Thorakotomie," Thoraxchirurgie Vaskulare Chirurgie, Band 15, Heft 2, Stuttgart, im Apr. 1967, pp. 199-203.

Rashkind, M.D., William J., "Historical Aspects of Interventional Cardiology: Past, Present, Future," Texas Heart Institute Journal, Interventional Cardiology, pp. 363-367.

Rashkind, M.D., William J., "Creationof an Atrial Septal Defect Withoput Thoracotomy," the Journal of the American Medical Association, vol. 196, No. 11, Jun. 13, 1966, pp. 173-174.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Serruys, P.W., et al., "Stenting of Coronary Arteries. Are we the Sorcerer's Apprentice?," European Heart Journal (1989) 10, 774-782, pp. 37-45, Jun. 13, 1989.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Urban, M.D., Philip, "Coronary Artery Stenting," Editions Médecine et Hygiène, Genève, 1991, pp. 5-47.

Uchida, Barry T., et al., "Modifications of Gianturco Expandable Wire Stents," AJR:150, May 1988, Dec. 3, 1987, pp. 1185-1187.

Wheatley, M.D., David J., "Valve Prostheses," Rob & Smith's Operative Surgery, Fourth Edition, pp. 415-424, Butterworths 1986.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Lutter, et al. "Percutaneous Valve Replacement: Current State and Future Prospects." The Society of Thoracic Surgeons. 2004.

* cited by examiner

PROSTHETIC HEART VALVE ASSEMBLY

CROSS-REFERENCE TO RELATED APPLICATIONS

This application is a continuation of U.S. patent application Ser. No. 17/203,611, filed Mar. 16, 2021, which is a continuation of U.S. patent application Ser. No. 16/238,344, filed Jan. 2, 2019, now U.S. Pat. No. 10,952,846, which is a continuation of U.S. patent application Ser. No. 15/683,611, filed Aug. 22, 2017, now U.S. Pat. No. 10,617,520, which is a continuation of U.S. patent application Ser. No. 14/584,903, filed Dec. 29, 2014, now U.S. Pat. No. 10,226,334, which is a continuation of U.S. patent application Ser. No. 13/660,875, filed Oct. 25, 2012, now abandoned, which is a continuation of U.S. patent application Ser. No. 12/113,418, filed May 1, 2008, now abandoned, each of which is incorporated by reference herein.

FIELD

The present disclosure concerns a prosthetic mitral heart valve and a method for implanting such a heart valve.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted.

Another known technique for implanting a prosthetic aortic valve is a transapical approach where a small incision is made in the chest wall of a patient and the catheter is advanced through the apex (i.e., bottom tip) of the heart. Transapical techniques are disclosed in U.S. Patent Application Publication No. 2007/0112422, which is hereby incorporated by reference. Like the transvascular approach, the transapical approach includes a balloon catheter having a steering mechanism for delivering a balloon-expandable prosthetic heart valve through an introducer to the aortic annulus. The balloon catheter includes a deflecting segment just proximal to the distal balloon to facilitate positioning of the prosthetic heart valve in the proper orientation within the aortic annulus.

The above techniques and others have provided numerous options for high-risk patients with aortic valve stenosis to avoid the consequences of open heart surgery and cardio-pulmonary bypass. While procedures for the aortic valve are well-developed, such procedures are not necessarily applicable to the mitral valve.

Mitral valve repair has increased in popularity due to its high success rates, and clinical improvements noted after repair. However, a significant percentage (i.e., about 33%) of patients still receive open-heart surgical mitral valve replacements due to calcium, stenosis, or anatomical limitations. There are a number of technologies aimed at making mitral repair a less invasive procedure. These technologies range from iterations of the Alfieri stitch procedure to coronary sinus-based modifications of mitral anatomy to subvalvular placations or ventricular remodeling devices, which would incidentally correct mitral regurgitation.

However, for mitral valve replacement, few less-invasive options are available. There are approximately 60,000 mitral valve replacements (MVR) each year and it is estimated that another 60,000 patients should receive MVR, but are denied the surgical procedure due to risks associated with the patient's age or other factors. One potential option for a less invasive mitral valve replacement is disclosed in U.S. Patent Application 2007/0016286 to Herrmann. However, the stent disclosed in that application has a claw structure for attaching the prosthetic valve to the heart. Such a claw structure could have stability issues and limit consistent placement of a transcatheter mitral replacement valve.

Accordingly, further options are needed for less-invasive mitral valve replacement.

SUMMARY

A prosthetic mitral valve assembly and method of inserting the same is disclosed.

In certain disclosed embodiments, the prosthetic mitral valve assembly has a flared upper end and a tapered portion to fit the contours of the native mitral valve. The prosthetic mitral valve assembly can include a stent or outer support frame with a valve mounted therein. The assembly is adapted to expand radially outwardly and into contact with the native tissue to create a pressure fit. With the mitral valve assembly properly positioned, it will replace the function of the native valve.

In other embodiments, the mitral valve assembly can be inserted above or below an annulus of the native mitral valve. When positioned below the annulus, the mitral valve assembly is sized to press into the native tissue such that the annulus itself can restrict the assembly from moving in an upward direction towards the left atrium. The mitral valve assembly is also positioned so that the native leaflets of the mitral valve are held in the open position.

In still other embodiments, when positioned above the annulus, prongs or other attachment mechanisms on an outer surface of the stent may be used to resist upward movement of the mitral valve assembly. Alternatively (or in addition), a tether or other anchoring member can be attached to the stent at one end and secured to a portion of the heart at another end in order to prevent movement of the mitral valve assembly after implantation. A tether may also be used to decrease the stress on the leaflets of the replacement valve and/or to re-shape the left ventricle.

In still other embodiments, the prosthetic mitral valve assembly can be inserted using a transapical procedure wherein an incision is made in the chest of a patient and in the apex of the heart. The mitral valve assembly is mounted in a compressed state on the distal end of a delivery catheter, which is inserted through the apex and into the heart. Once inside the heart, the valve assembly can be expanded to its functional size and positioned at the desired location within the native valve. In certain embodiments, the valve assembly can be self-expanding so that it can expand to its functional size inside the heart when advanced from the distal end of a delivery sheath. In other embodiments, the valve assembly can be mounted in a compressed state on a balloon of the delivery catheter and is expandable by inflation of the balloon.

These features and others of the described embodiments will be more readily apparent from the following detailed description, which proceeds with reference to the accompanying drawings.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but can optionally contain C or other components other than A and B. A device that includes or comprises A or B may contain A or B or A and B, and optionally one or more other components such as C.

Figure 1:
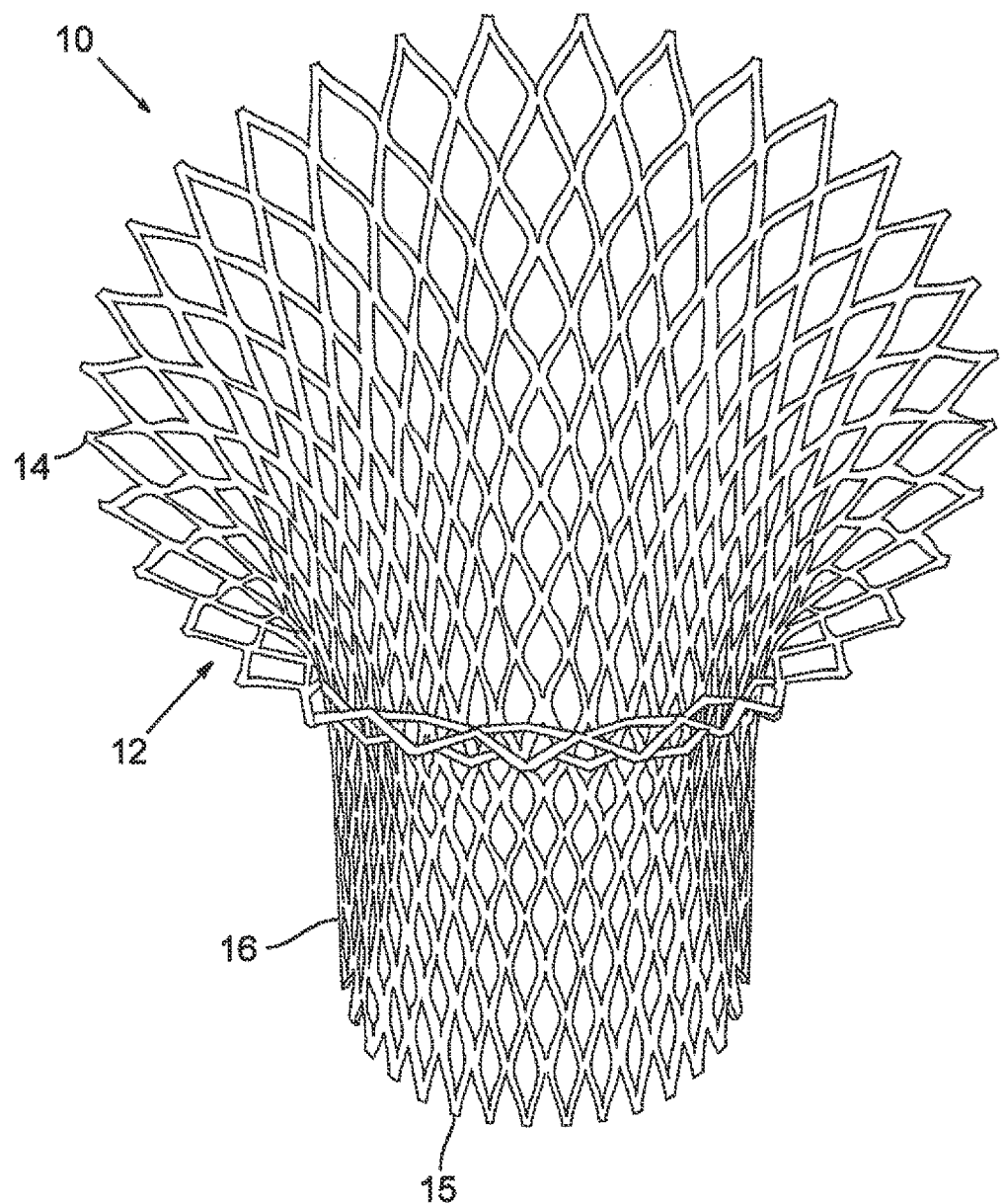
FIG. 1 is a perspective view of a stent used in certain embodiments of a mitral valve assembly.

FIG. 1 is a perspective view of a stent 10 configured for placement in a native mitral valve. The stent in this embodiment includes an upper portion 12 having an enlarged or flared end 14 that tapers to a lower portion 16 having a reduced diameter. The stent generally has a bell shape or a truncated conical shape, but other shapes can be used. The stent 10 can have a continuous taper from the flared end 14 to the lower end 15. As described below, at least the upper portion desirably tapers in a direction from the upper end to the lower end 15 so as to generally conform to the contours of the native leaflets to assist in securing the stent within the native valve. In some embodiments, the portion of the stent extending below the native leaflets can have a generally cylindrical shape or could further taper. Additionally, the length of the stent 10 can vary. In some embodiments the stent can be between 15-50 mm in length. For example, specific testing has been performed on stents having lengths of 24 mm and 46 mm in length. A circumference of the stent 10 varies along a length thereof, but is generally sized for receiving a bicuspid or tricuspid valve. An example circumference of the stent at a point in the upper portion is 30 mm, but other sizes can be used depending on the desired valve. The stent can be a self-expanding stent formed from a shape memory material, such as, for example, Nitinol. In the illustrated embodiment, the stent is formed from multiple somewhat arcuate—shaped fibers extending along the length of the stent with approximately half of the fibers bent in a first direction and half of the fibers bent in a second direction to create a crisscross pattern. As explained further below, the stent can be delivered in a radially-compressed state using an introducer, such that after reaching the treatment site, it is advanced out of the distal end of the introducer and expands to its functional size in a relaxed state in contact with the surrounding tissue. A specific example of such a technique is shown and described below in relation to FIGS. 8A-8D.

In other embodiments, the stent 10 can be a balloon-expandable stent. In such a case, the stent can be formed from stainless steel or any other suitable materials. The balloon-expandable stent can be configured to be crimped to a reduced diameter and placed over a deflated balloon on the distal end portion of an elongate balloon catheter, as is well-understood in the art.

The flared end 14 of the stent 10 helps to secure the stent above or below the annulus of the native mitral valve (depending on the procedure used), while the tapered portion is shaped for being held in place by the native leaflets of the mitral valve.

Figure 2A:
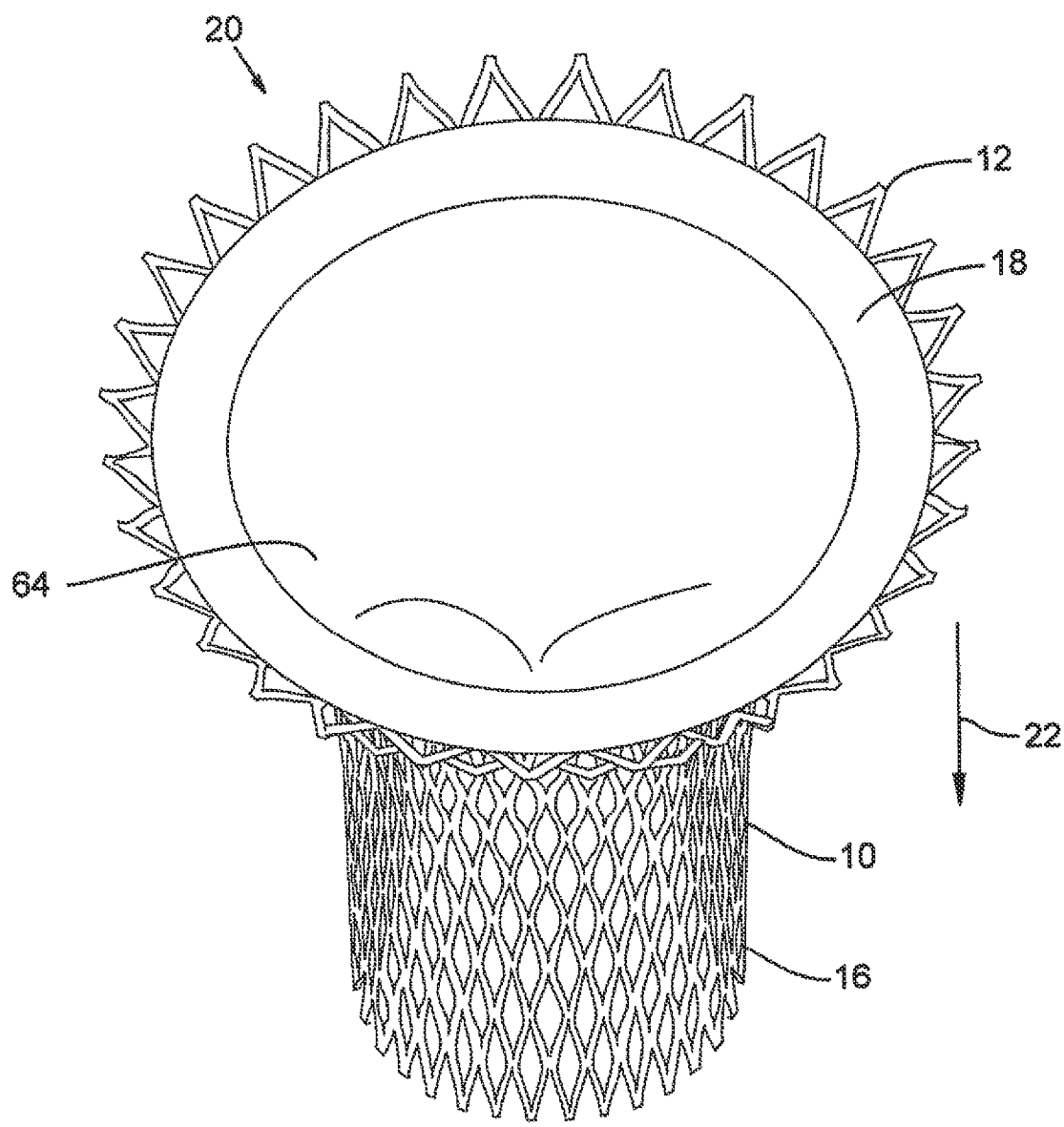
FIGS. 2A and 2B are a perspective views an embodiment of a mitral valve assembly using the stent of FIG. 1, as viewed from the top and bottom, respectively, of the assembly.
Figure 2B:
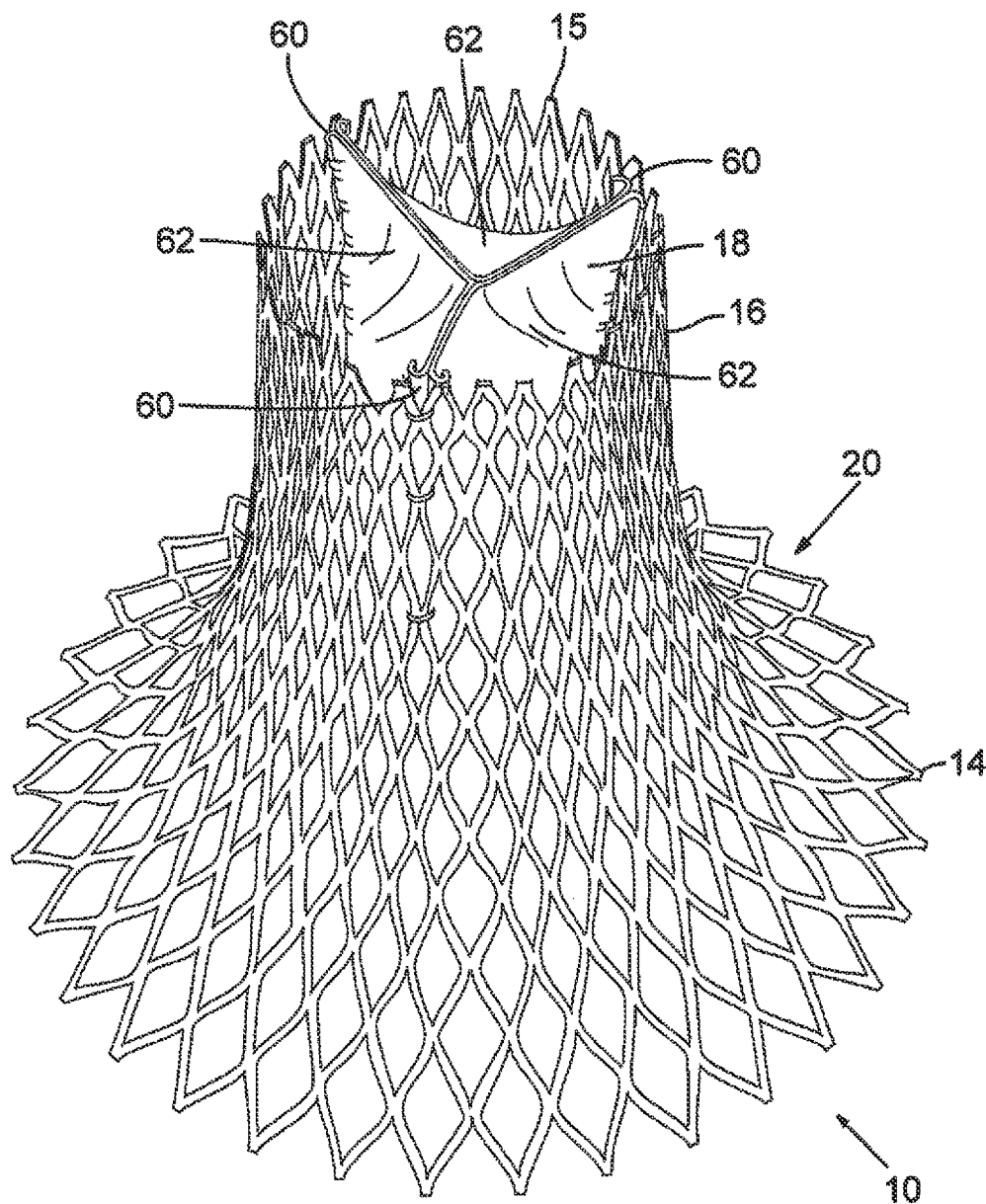

FIGS. 2A and 2B are perspective views of the stent 10 with a valve 18 inserted therein to form a mitral valve assembly 20. The valve 18 can have a leafed-valve configuration, such as a bicuspid valve configuration or the tricuspid valve configuration shown in the illustrated embodiment. As shown in FIG. 2B, the valve 18 can be formed from three pieces of flexible, pliant material connected to each other at seams 60 (also referred to as commissure tabs) to form collapsible leaflets 62 and a base, or upper end, portion 64. The valve 18 can be connected to the stent 10 at the seams 60 using, for example, sutures or other suitable connection techniques well-known in the art. Alternatively, the valve 18 can be a mechanical type valve, rather than a leafed type valve.

The valve 18 can be made from biological matter, such as natural tissue, pericardial tissue (e.g., bovine, porcine or equine pericardium), a harvested natural valve, or other biological tissue. Alternatively, the valve can be made from biocompatible synthetic materials (e.g., biocompatible polymers), which are well known in the art. The valve can be shaped to fit the contours of the stent so as to have a flared upper end portion having an upper circumference larger than a lower circumference at the lower end of the valve. Blood flow through the valve proceeds in a direction from the upper portion 12 to the lower portion 16, as indicated by arrow 22 (FIG. 2A).

Figure 3:
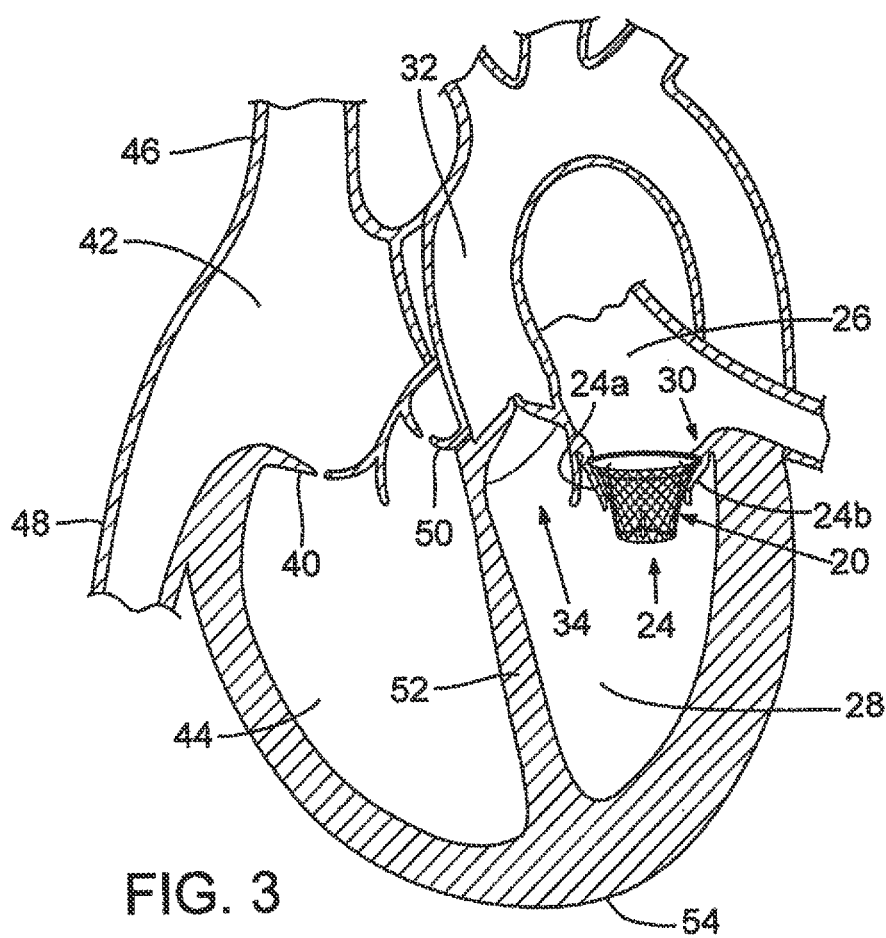
FIG. 3 is a cross-sectional view of a heart with the mitral valve assembly of FIG. 2 implanted within the native mitral valve.

FIG. 3 shows a cross-sectional view of a heart with the prosthetic mitral-valve assembly inserted into the native mitral valve. For purposes of background, the four-chambered heart is explained further. On the left side of the heart, the native mitral valve 24 is located between the left atrium 26 and left ventricle 28. The mitral valve generally comprises two leaflets, an anterior leaflet 24a and a posterior leaflet 24b. The mitral valve leaflets are attached to a mitral valve annulus 30, which is defined as the portion of tissue surrounding the mitral valve orifice. The left atrium 26 receives oxygenated blood from the pulmonary veins. The oxygenated blood that is collected in the left atrium 26 enters the left ventricle 28 through the mitral valve 24.

Contraction of the left ventricle 28 forces blood through the left ventricular outflow tract and into the aorta 32. The aortic valve 34 is located between the left ventricle 28 and the aorta 32 for ensuring that blood flows in only one direction (i.e., from the left ventricle to the aorta). As used herein, the left ventricular outflow tract (LVOT) is intended to generally include the portion of the heart through which blood is channeled from the left ventricle to the aorta.

On the right side of the heart, the tricuspid valve 40 is located between the right atrium 42 and the right ventricle 44. The right atrium 42 receives blood from the superior vena cava 46 and the inferior vena cava 48. The superior vena cava 46 returns de-oxygenated blood from the upper part of the body and the inferior vena cava 48 returns de-oxygenated blood from the lower part of the body. The right atrium 42 also receives blood from the heart muscle itself via the coronary sinus. The blood in the right atrium 42 enters into the right ventricle 44 through the tricuspid valve 40. Contraction of the right ventricle forces blood through the right ventricle outflow tract and into the pulmonary arteries. The pulmonic valve 50 is located between the right ventricle 44 and the pulmonary trunk for ensuring that blood flows in only one direction from the right ventricle to the pulmonary trunk.

The left and right sides of the heart are separated by a wall generally referred to as the septum 52. The portion of the septum that separates the two upper chambers (the right and left atria) of the heart is termed the atrial (or interatrial) septum while the portion of the septum that lies between the two lower chambers (the right and left ventricles) of the heart is called the ventricular (or interventricular) septum. A healthy heart has a generally conical shape that tapers from a base to an apex 54.

As shown in FIG. 3, the mitral valve assembly 20 is positioned such that the flared end 14 of the upper portion 12 is adjacent the annulus 30 of the native mitral valve 24, while the leaflets of the native valve bear against and hold the tapered upper end portion 12 of the mitral valve assembly. The prosthetic mitral valve assembly of FIG. 3 is preferably positioned with the flared end 14 above or just below an annulus 30 of the native mitral valve. The valve assembly is configured to form a "pressure fit" with the surrounding native valve tissue; that is, the outward radial pressure of the stent bears against the surrounding tissue to assist in retaining the valve assembly in place.

Figure 4:
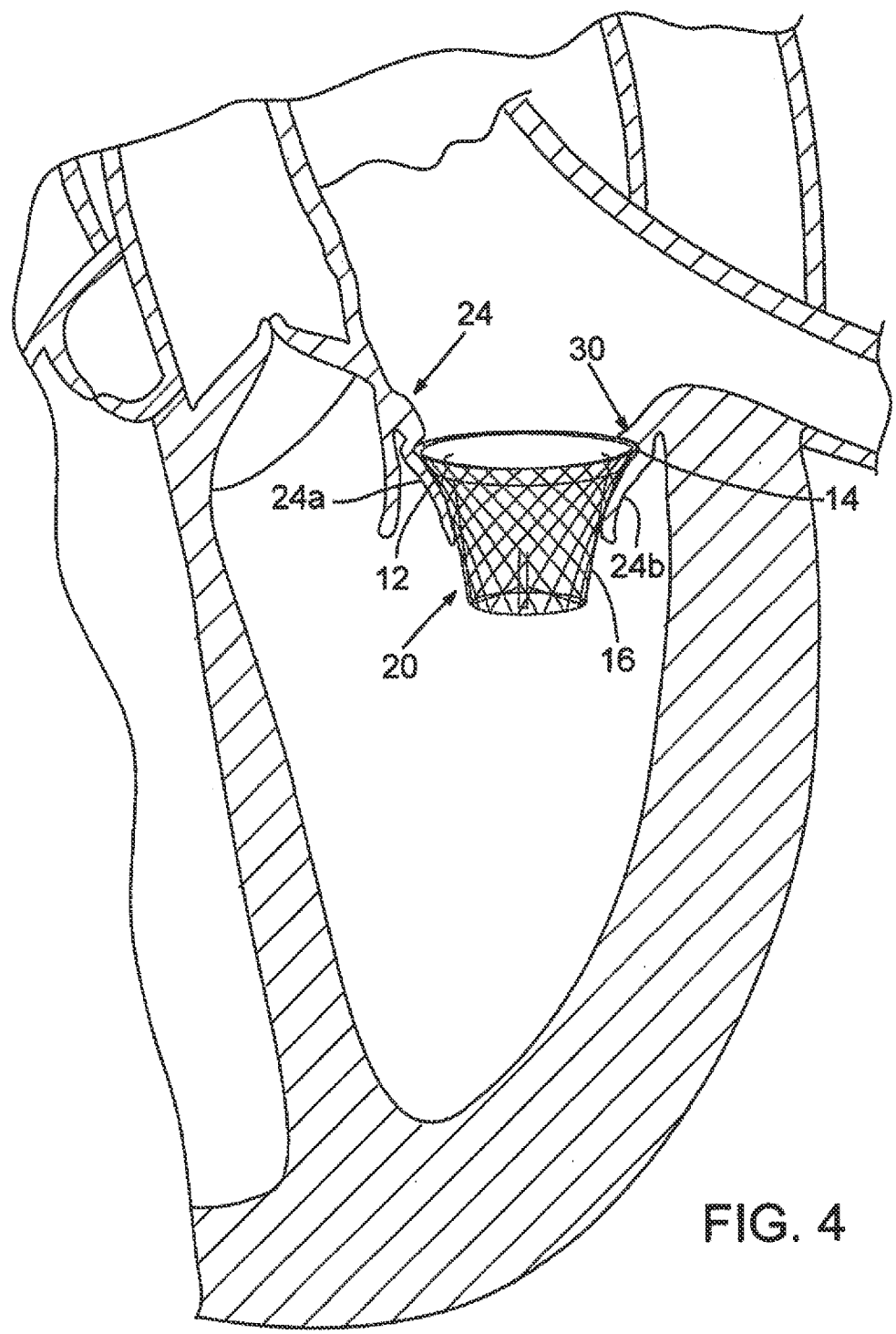
FIG. 4 is an enlarged cross-sectional view of a heart with an embodiment of the mitral valve assembly implanted below an annulus of the native mitral valve.

FIG. 4 is enlarged view of the mitral valve assembly 20 positioned below the annulus 30 of the native mitral valve 24. In particular, the flared end 14 of the stent is tucked under the annulus 30 of the native mitral valve (under the insertion point of the mitral leaflets to the left atrium), but on top of the mitral valve leaflets 24a, 24b. When deployed in this position, the mitral valve assembly exerts sufficient radial pressure outwardly to press into the native tissue, as the shape-memory material exerts an outward radial force to return the assembly to its expanded shape. As a result of the positioning of the flared end 14, the annulus 30 protrudes slightly inwardly past the flared end of the stent and acts as an annular mechanical stop preventing upward movement of the mitral valve assembly 20. The amount of outward radial pressure exerted by the mitral valve assembly 20 depends partly on the size of the stent and the type of shape-memory material used. The stent size can depend on the particular patient and the desired amount of pressure needed to hold the prosthetic mitral valve in place. The tapered upper portion 12 of the mitral valve assembly 20 desirably is shaped to fit the contours of the native mitral valve leaflets 24a, 24b, which bear against the outer surface of the stent and prevent downward motion of the assembly. Thus, due to the unique shape of the mitral valve assembly 20, it can be held in place solely by the pressure exerted by the stent radially outwardly against the surrounding tissue without the use of hooks, prongs, clamps or other grasping device.

When properly positioned, the valve assembly avoids or at least minimizes paravalvular leakage. In tests performed on a porcine heart, approximately two pounds of force or greater were applied to stents in the left atrial direction with little or no dislodgement, movement or disorientation.

Figure 5:
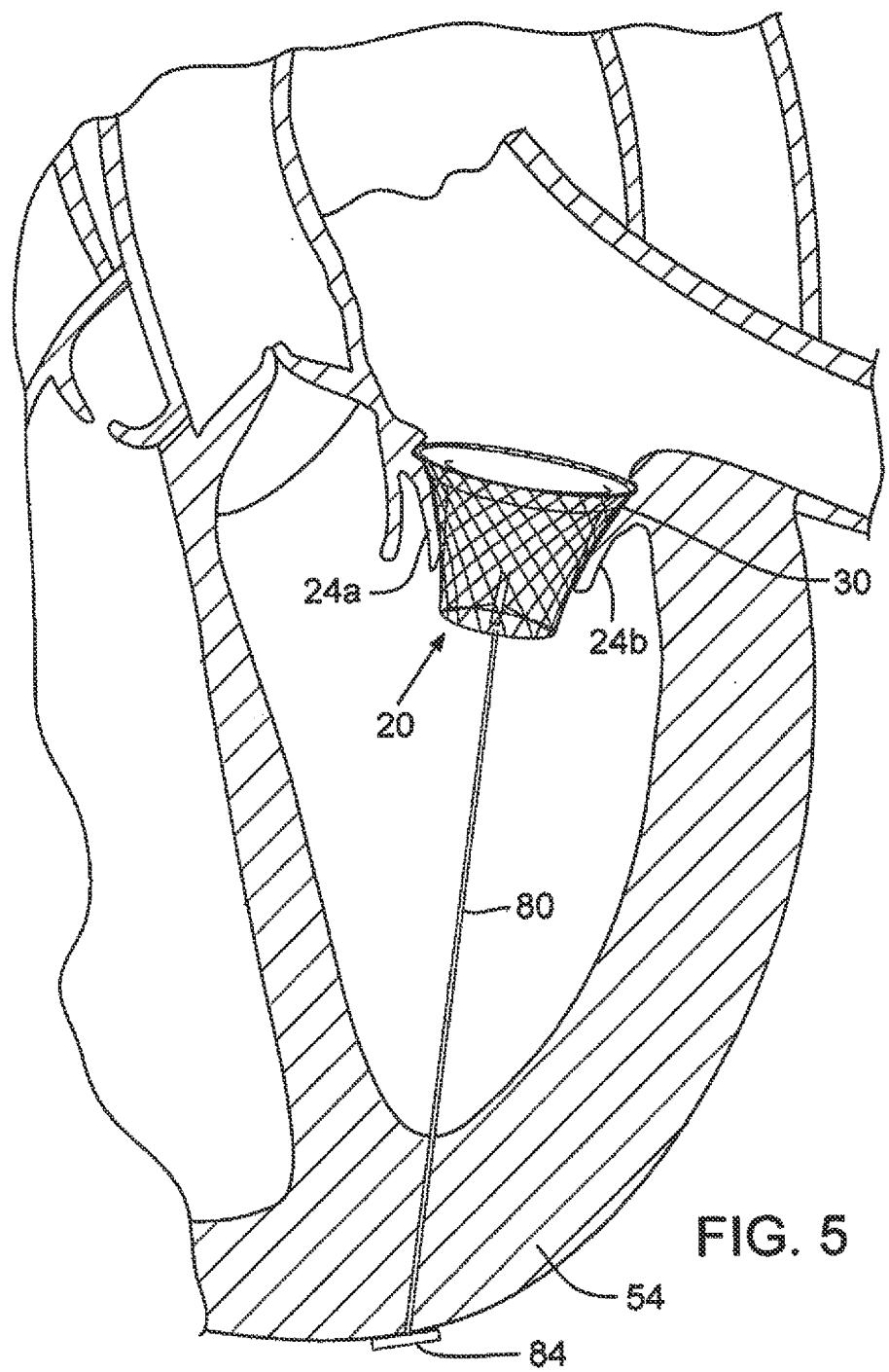
FIG. 5 is an enlarged cross-sectional view of a heart with an embodiment of the mitral valve assembly implanted within the native mitral valve wherein a tether is attached to the stent for preventing migration of the mitral valve assembly.

FIG. 5 shows an alternative positioning of the mitral valve assembly. In this position, the mitral valve assembly 20 can be secured above the native mitral valve annulus 30. The mitral valve leaflets 24a, 24b still prevent downward movement of the mitral valve assembly. However, to assist in preventing upward movement, the mitral valve assembly 20 can be anchored using a tether 80 coupled between a lower portion of the mitral valve assembly (such as by being tied to the stent) and a portion of the heart (e.g., an opposing wall). In the particular embodiment shown, the tether 80 extends through the apex 54 of the heart and is secured in place by an enlarged head portion 84 connected to the lower end of the tether outside of the apex. The tether and/or head portion can be formed of a bioresorbable material so that it eventually dissolves after the stent has grown into the wall of the native mitral valve.

Figure 6:
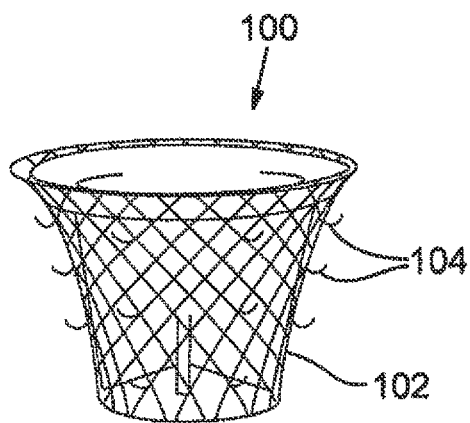
FIG. 6 is a perspective view of a mitral valve assembly having external anchoring members to assist in securing the mitral valve assembly to the surrounding tissue.

FIG. 6 shows another embodiment of a mitral valve assembly 100 that may be used with supra-annular positioning. In particular, an outer surface of a stent 102 includes anchoring members, such as, for example, prongs 104 in the form of upwardly bent hooks, that can penetrate the surrounding tissue to prevent upward migration of the assembly 100 when in place. The anchoring members may be made from the same material as the stent, but alternative materials may also be used.

Figure 7:
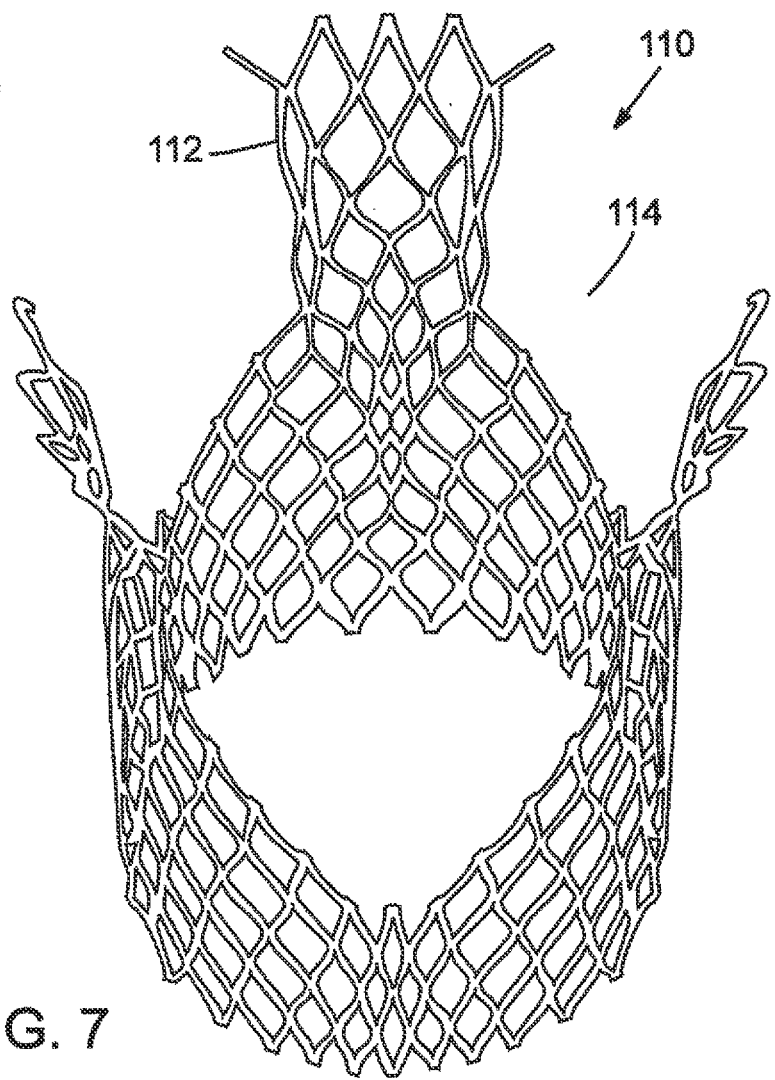
FIG. 7 is a perspective view of an embodiment of a stent having a scalloped end portion.

FIG. 7 shows another embodiment of a stent 110 that can be used. In this embodiment, an upper portion 112 of the stent is scalloped (i.e., the upper edge has one or more indented or cut-out portions 114). In some patients, the pressure exerted by the upper rim of the stent on the anterior mitral leaflet can displace the mitral curtain and anterior leaflet toward the left ventricular outflow track. The stent can be deployed such that the anterior leaflet is generally positioned within a cutout (scalloped) portion of the stent. In this manner, the scalloped stent 110 reduces the pressure on the leaflet to ensure there is no alteration of blood flow in the left ventricle.

FIGS. 8A-8D depict an embodiment of a transapical procedure for inserting the prosthetic mitral valve assembly into the native mitral valve. The replacement procedure is typically accomplished by implanting the prosthetic mitral valve assembly directly over the native leaflets, which are typically calcified. In this manner, the native leaflets 24a, 24b can assist in securing the mitral valve assembly in place.

First, an incision is made in the chest of a patient and in the apex 54 of the patient's heart. A guide wire 120 is inserted through the apex 54 and into the left ventricle. The guide wire 120 is then directed up through the mitral valve 24 and into the left atrium 26. An introducer 122 is advanced over the guide wire into the left atrium (see FIGS. 8A and 8B). A delivery catheter 124 is inserted through the introducer (see FIG. 8B). A prosthetic valve assembly 20 is retained in a crimped state on the distal end portion of the delivery catheter as the valve assembly and delivery catheter are advanced through the introducer. In one variation, the introducer 122 is formed with a tapered distal end portion 123 to assist in navigating through the chordae tendinae. The delivery catheter 124 likewise can have a tapered distal end portion 126.

Figure 8A:
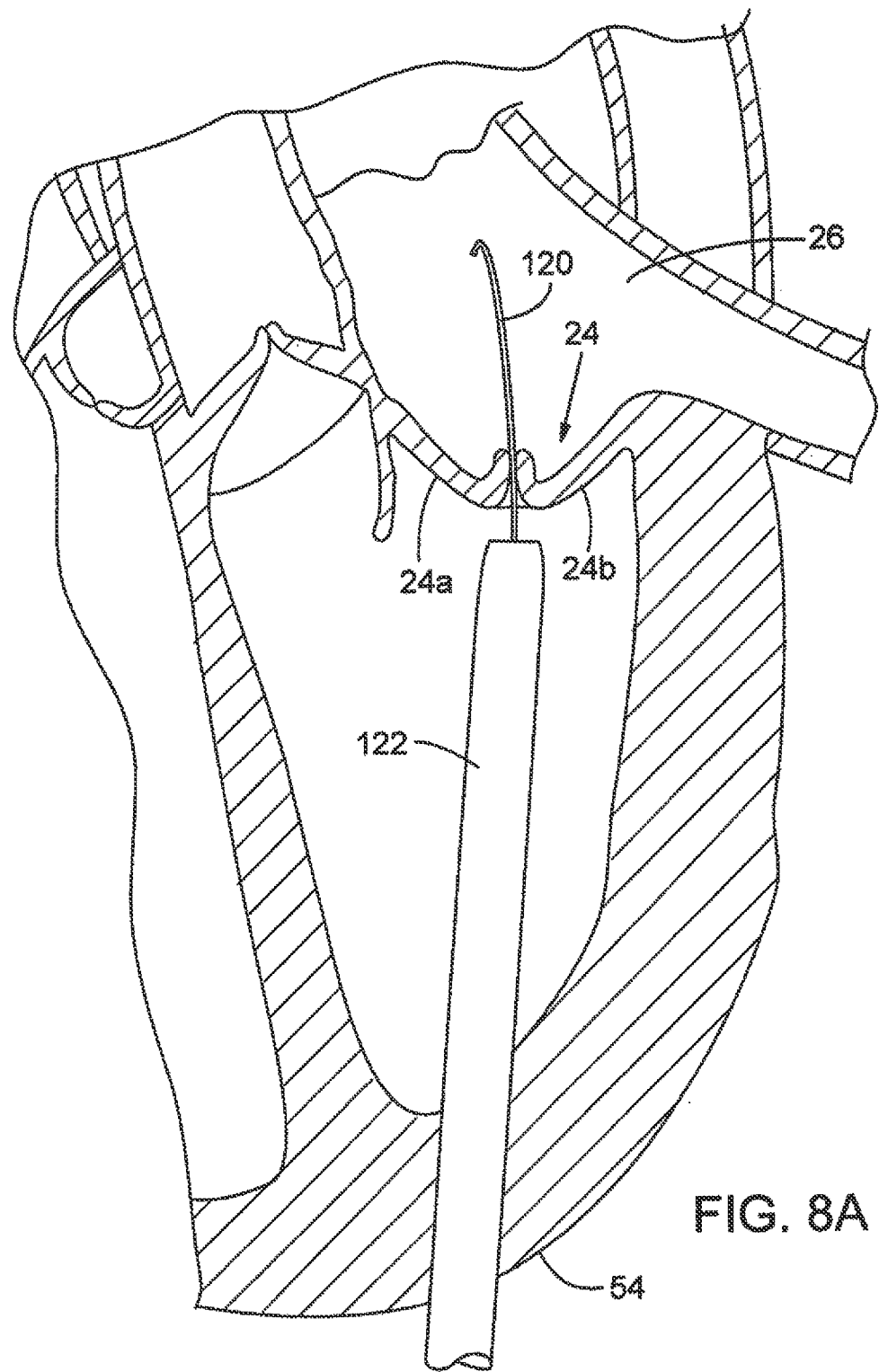
FIGS. 8A-8D are cross-sectional views showing an embodiment of the mitral valve assembly inserted using a transapical procedure.
Figure 8B:
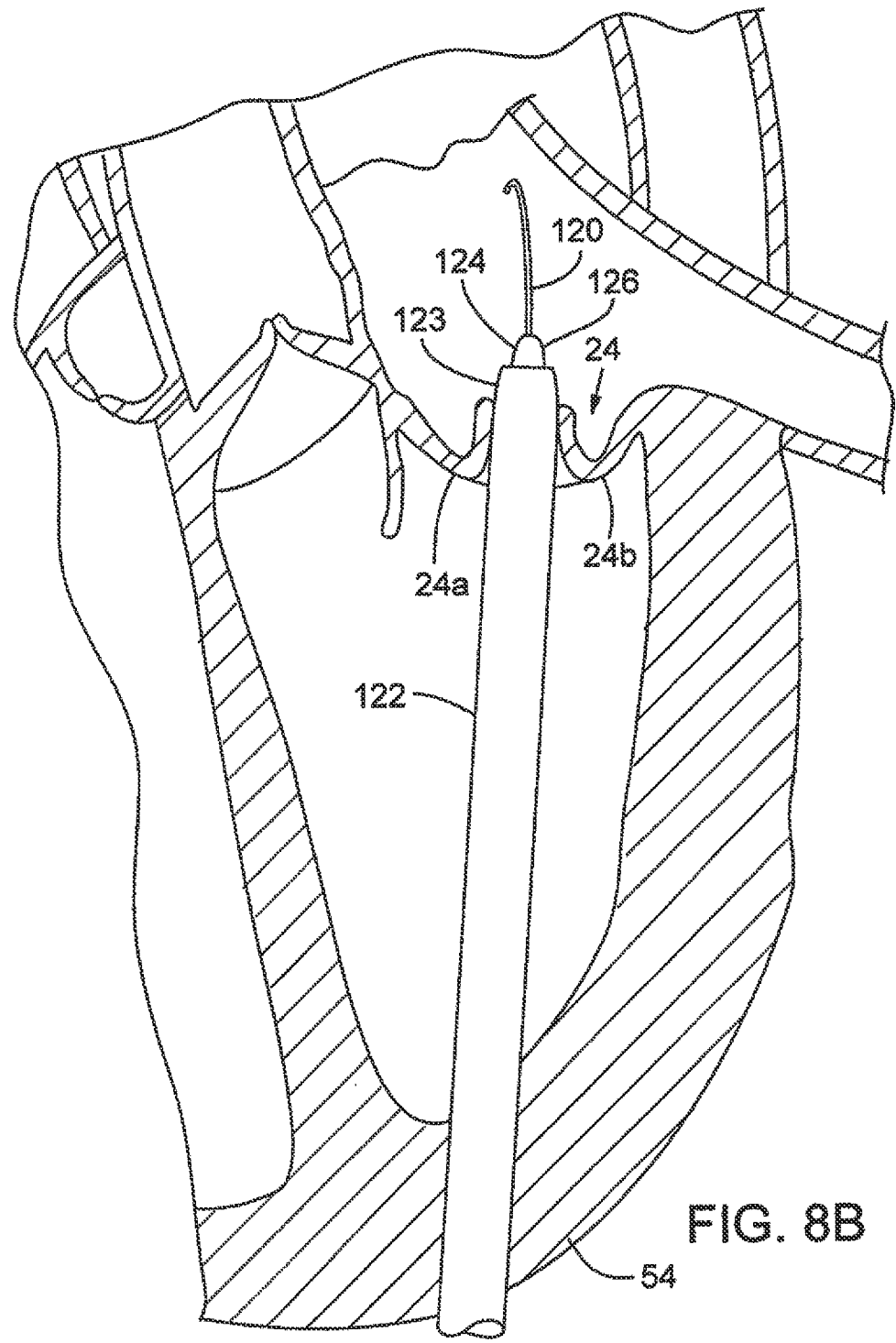
Figure 8C:
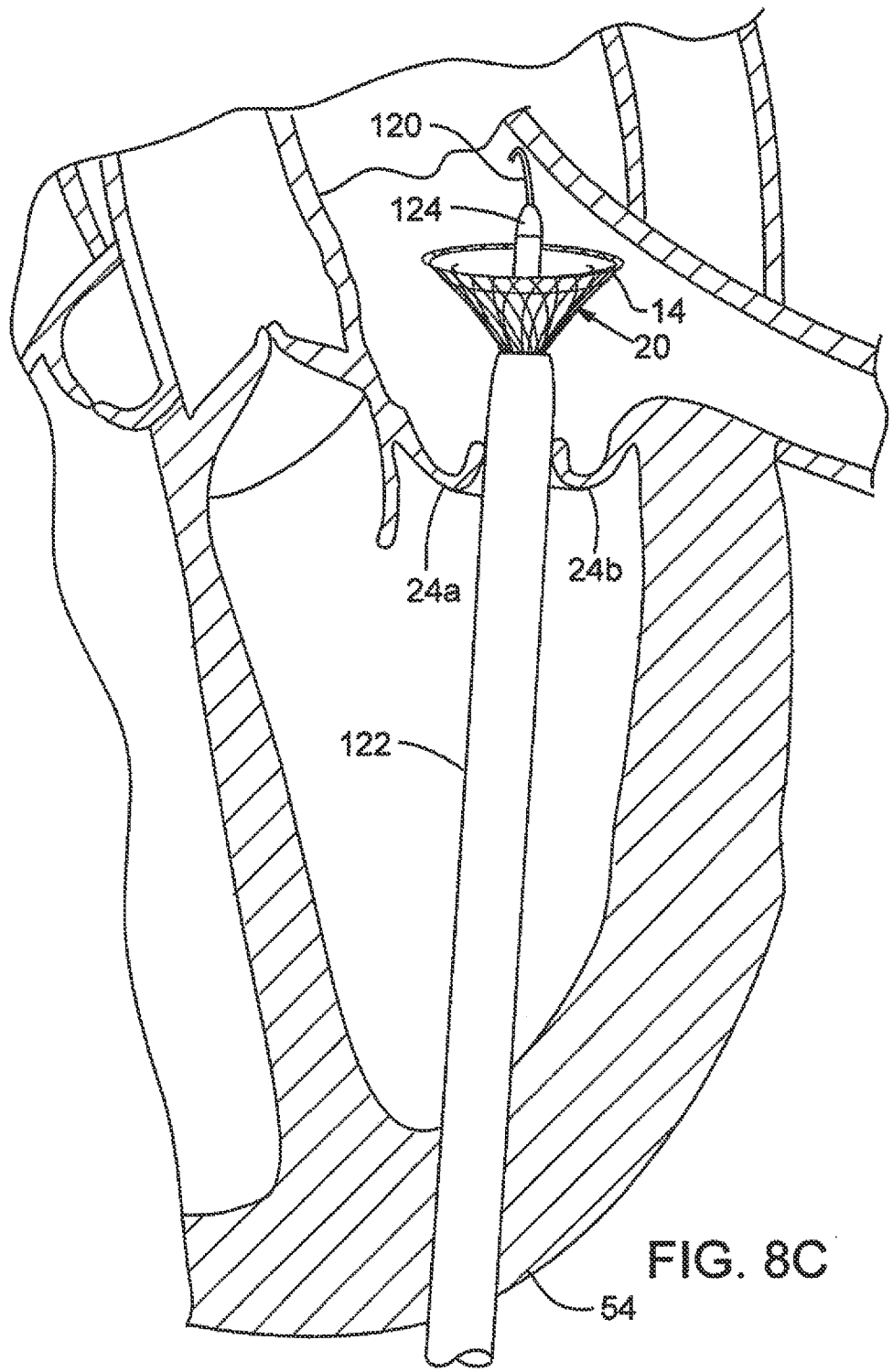
Figure 8D:
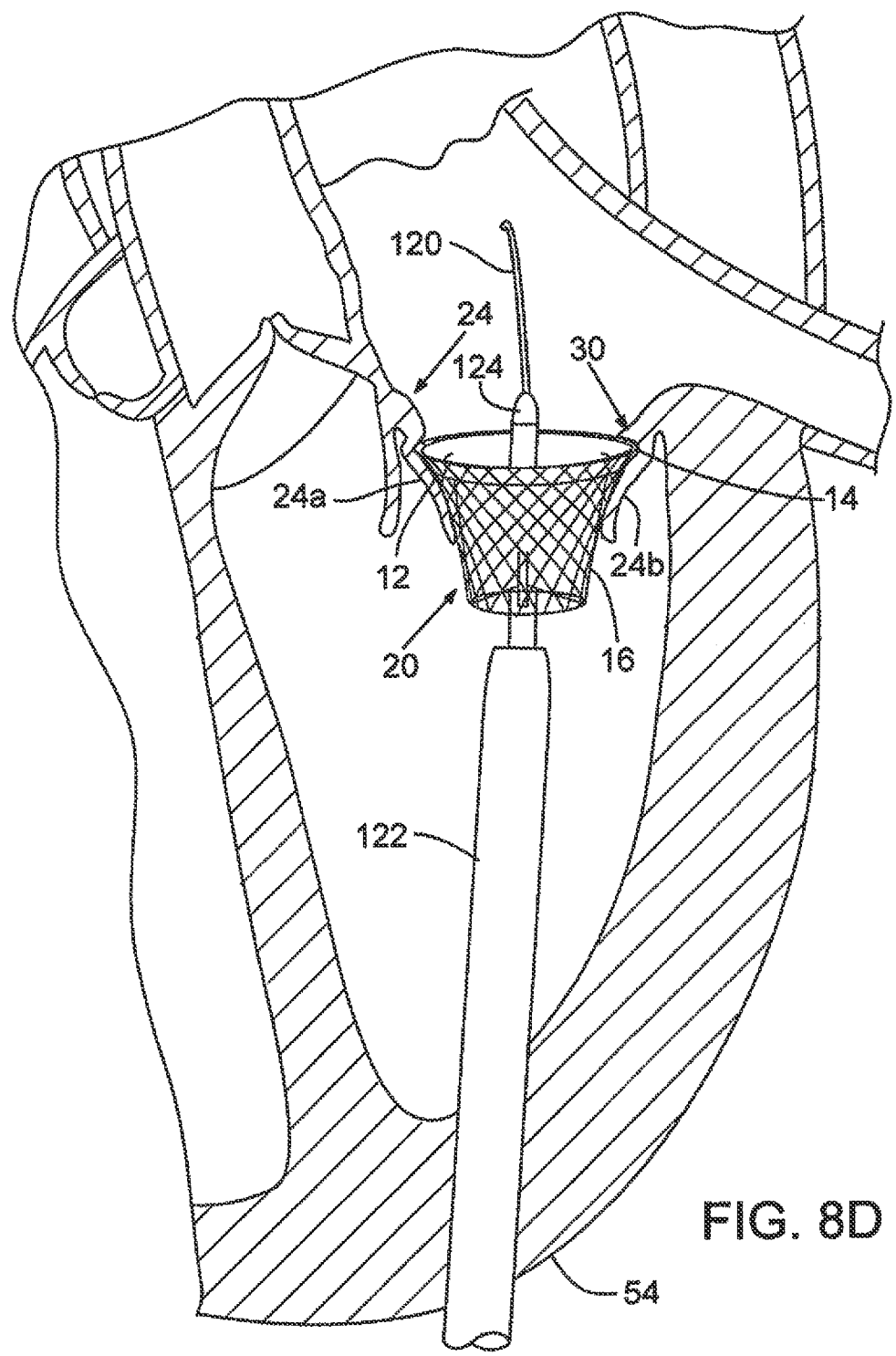

In FIG. 8C, the introducer 122 is retracted relative to the mitral valve assembly 20 for deploying the mitral valve assembly from the distal end of the introducer. To pull the valve assembly 20 into position at the intended implantation site, the valve assembly desirably is partially advanced out of the introducer to expose the flared upper end portion 12, while the remainder of the valve assembly remains compressed within the introducer (as shown in FIG. 8C). As shown, the flared end portion expands when advanced from the distal end of the introducer. The delivery catheter 124 and the introducer 122 can then be retracted together to pull the flared end into the desired position (e.g., just below the annulus of the native valve). Thereafter, the introducer can be further retracted relative to the delivery catheter to advance the remaining portion of the valve assembly 20 from the introducer, thereby allowing the entire assembly to expand to its functional size, as shown in FIG. 8D. The introducer and catheter can then be withdrawn from the patient.

Alternatively, the mitral valve assembly can be fully expanded directly in place at the implantation site by first aligning the valve assembly at the implantation site and then retracting the introducer relative to the delivery catheter to allow the entire valve assembly to expand to its functional size. In this case, there is no need to pull the mitral valve assembly down into the implantation site. Additional details of the transapical approach are disclosed in U.S. Patent Application Publication No. 2007/0112422 (mentioned above).

In another embodiment, the valve assembly 20 can be mounted on an expandable balloon of a delivery catheter and expanded to its functional size by inflation of the balloon. When using a balloon catheter, the valve assembly can be advanced from the introducer to initially position the valve assembly in the left atrium 26. The balloon can be inflated to fully expand the valve assembly. The delivery catheter can then be retracted to pull the expanded valve assembly into the desired implantation site (e.g., just below the annulus of the native valve). In another embodiment, the balloon initially can be partially inflated to partially expand the valve assembly in the left atrium. The delivery catheter can then be retracted to pull the partially expanded valve into the implantation site, after which the valve assembly can be fully expanded to its functional size.

Mitral regurgitation can occur over time due to the lack of coaptation of the leaflets in the prosthetic mitral valve assembly. The lack of coaptation in turn can lead to blood being regurgitated into the left atrium, causing pulmonary congestion and shortness of breath. To minimize regurgitation, the leaflets of the valve assembly can be connected to one or more tension members that function as prosthetic chordae tendinae.

Figure 9:
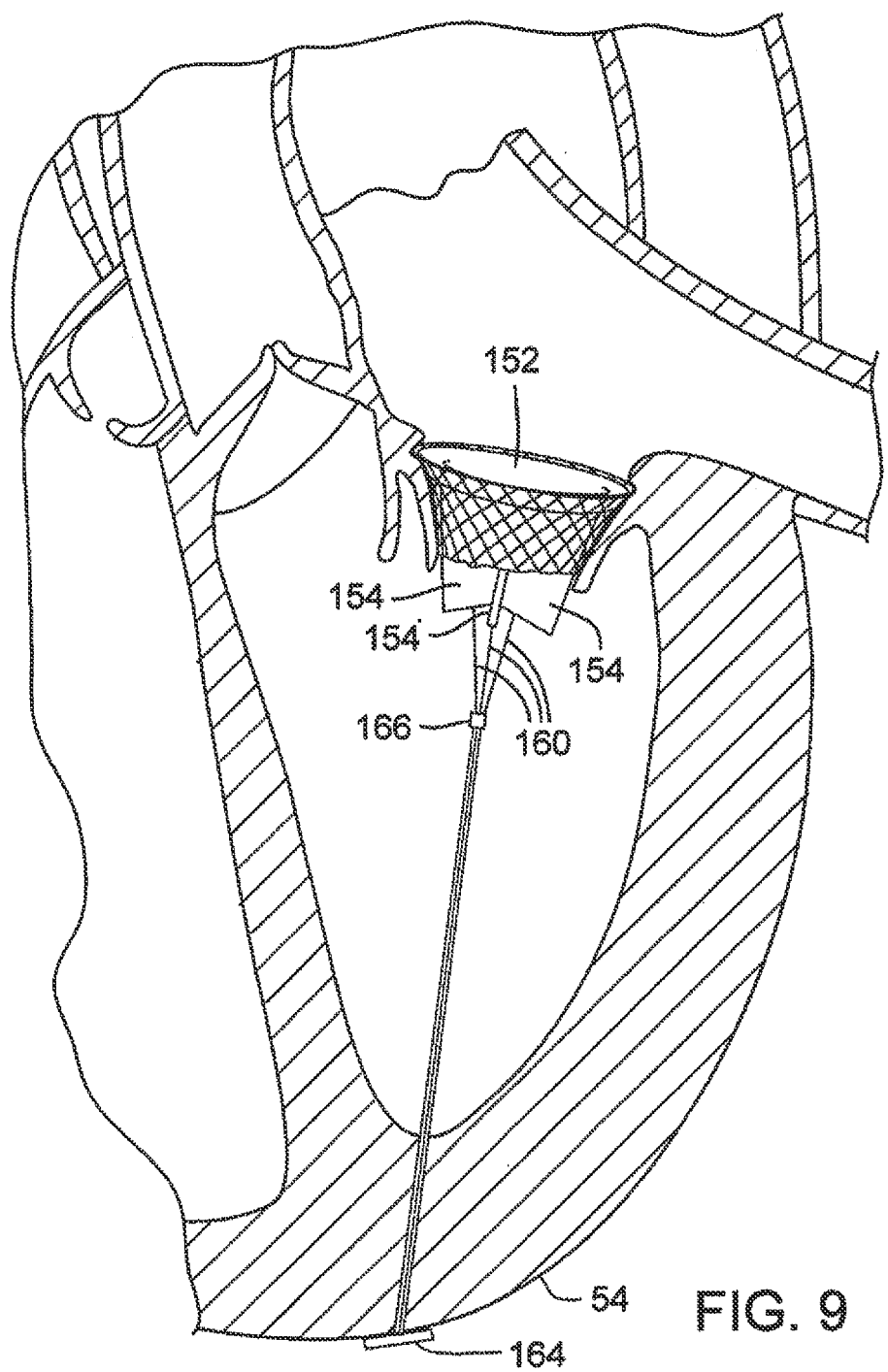
FIG. 9 is a perspective view of an embodiment of a prosthetic valve assembly having tensioning members coupled to prosthetic leaflets of the valve to simulate chordae tendinae.

FIG. 9, for example, shows an embodiment comprising a prosthetic mitral valve assembly 152 having leaflets 154. Each leaflet 154 can be connected to a respective tension member 160, the lower ends of which can be connected at a suitable location on the heart. For example, the lower end portions of tension members 160 can extend through the apex 54 and can be secured at a common location outside the heart. Tension members may be attached to or through the papillary muscles. The lower ends of tension members can be connected to an enlarged head portion, or anchor, 164, which secures the tension members to the apex. Tension members 160 can extend through a tensioning block 166. The tensioning block 166 can be configured to slide upwardly and downwardly relative to tension members 160 to adjust the tension in the tensioning members. For example, sliding the tensioning block 166 upwardly is effective to draw the upper portions of the tension members closer together, thereby increasing the tension in the tension members. The tensioning block 166 desirably is configured to be retained in place along the length of the tension members, such as by crimping the tensioning block against the tension members, once the desired tension is achieved. The tension members can be made of any suitable biocompatible material, such as traditional suture material, GORE-TEX®, or an elastomeric material, such as polyurethane. The tension members 160 further assist in securing the valve assembly in place by resisting upward movement of the valve assembly and prevent the leaflets 154 from everting so as to minimize or prevent regurgitation through the valve assembly. As such, the tethering de-stresses the moveable leaflets, particularly during ventricular systole (i.e., when the mitral valve is closed). Alternatively or in addition, the stent 10 can be connected to one or more tension members 160 for stabilizing the mitral valve assembly during the cyclic loading caused by the beating heart.

Figure 10:
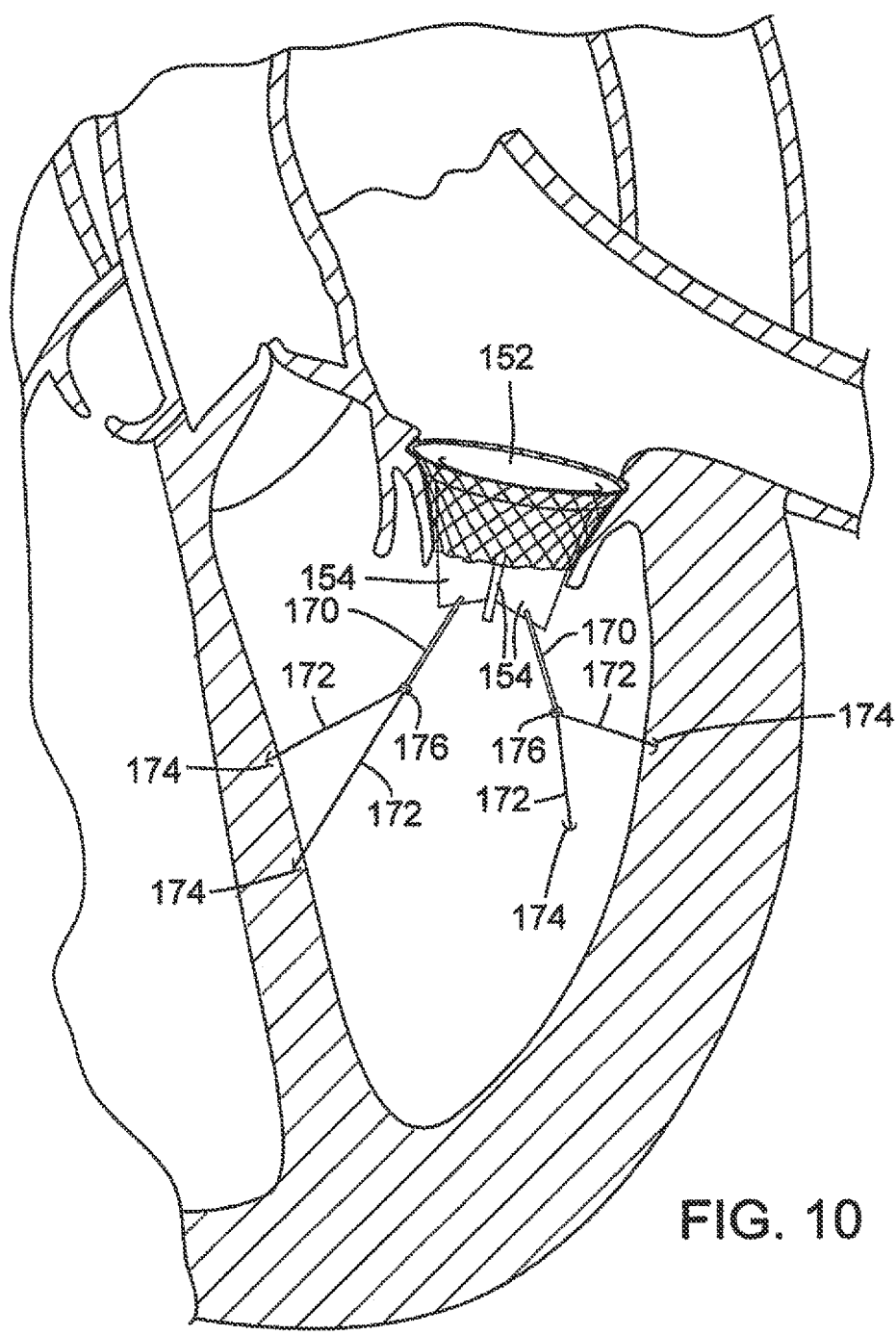
FIG. 10 is a perspective view of a prosthetic valve assembly having tensioning members, according to another embodiment.

FIG. 10 shows another embodiment of a mitral valve assembly 152 having prosthetic chordae tendinae. The prosthetic chordae tendinae comprise first and second tension members 170 connected to a respective leaflet 154 of the valve assembly. As shown, the lower end portions 172 of each tension member 170 can be connected at spaced apart locations to the inner walls of the left ventricle, using, for example, anchor members 174. A slidable tensioning block 176 can be placed over each tension member 170 for adjusting the tension in the corresponding tension member. In certain embodiments, each tension member 170 can comprise a suture line that extends through a corresponding leaflet 154 and has its opposite ends secured to the ventricle walls using anchor members 174.

In particular embodiments, the anchor member 174 can have a plurality of prongs that can grab, penetrate, and/or engage surrounding tissue to secure the device in place. The prongs of the anchor member 174 can be formed from a shape memory material to allow the anchor member to be inserted into the heart in a radially compressed state (e.g., via an introducer) and expanded when deployed inside the heart. The anchor member can be formed to have an expanded configuration that conforms to the contours of the particular surface area of the heart where the anchor member is to be deployed, such as described in co-pending application Ser. No. 11/750,272, published as US 2007/0270943 A1, which is incorporated herein by reference. Further details of the structure and use of the anchor member are also disclosed in co-pending application Ser. No. 11/695,583 to Rowe, filed Apr. 2, 2007, which is incorporated herein by reference.

Alternative attachment locations in the heart are possible, such as attachment to the papillary muscle (not shown). In addition, various attachment mechanisms can be used to attach tension members to the heart, such as a barbed or screw-type anchor member. Moreover, any desired number of tension members can be attached to each leaflet (e.g., 1, 2, 3 . . . etc.). Further, it should be understood that tension members (e.g., tension members 160 or 170) can be used on any of the embodiments disclosed herein.

As discussed above, FIGS. 9-10 show the use of tension members that can mimic the function of chordae. The tethers can have several functions including preventing the valve from migrating into the left atrium, de-stressing the leaflets by preventing eversion, and preserving ventricular function by maintaining the shape of the left ventricle. In particular, the left ventricle can lose its shape over time as the natural chordae become stretched or break. The artificial chordae can help to maintain the shape. Although FIGS. 9 and 10 show a tricuspid valve, a bicuspid valve can be used instead. Particular bicuspid valves are shown in FIGS. 12-16.

Figure 11:
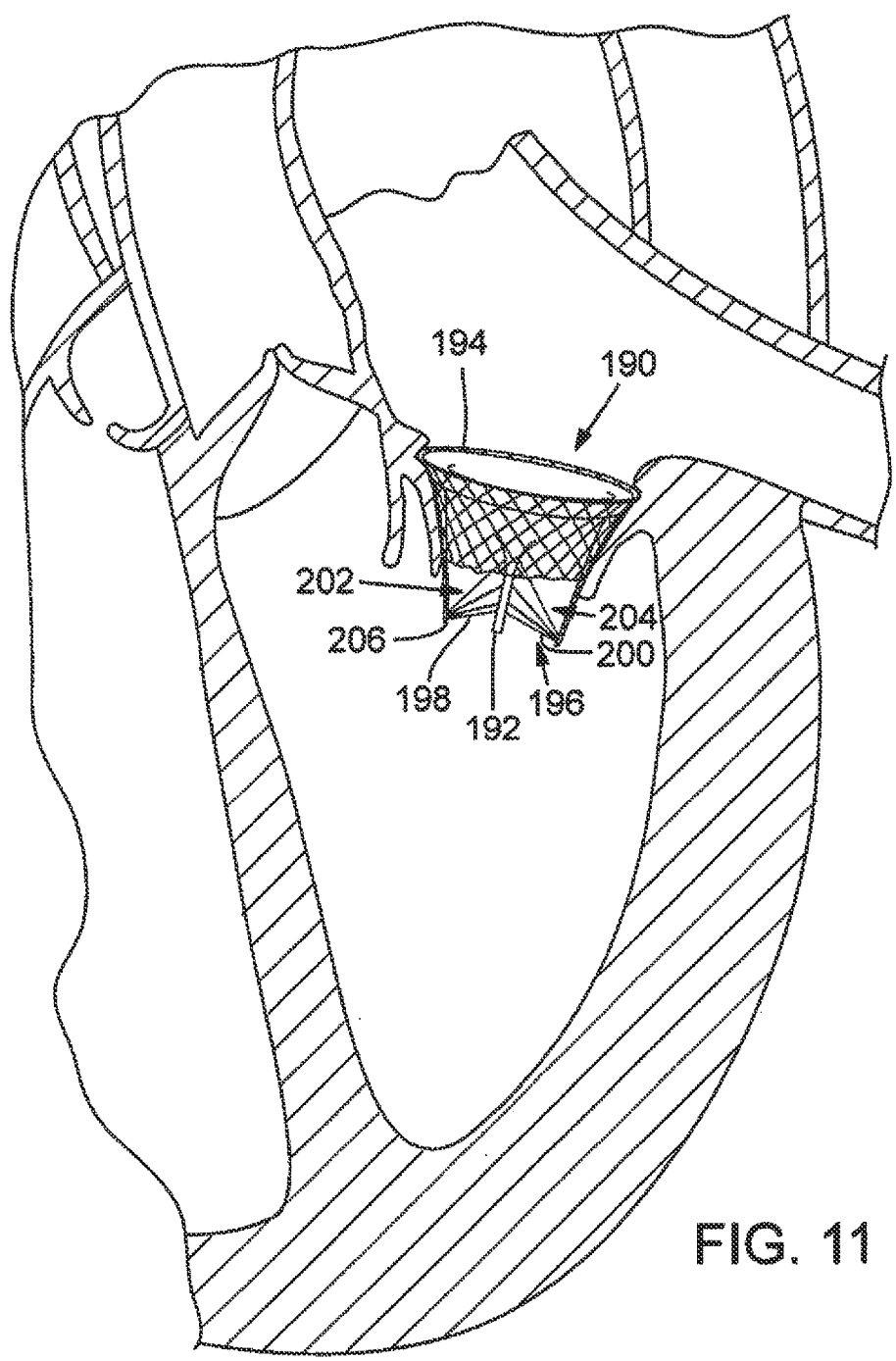
FIG. 11 is a perspective view of a prosthetic valve assembly having tensioning members, according to another embodiment.

FIG. 11 shows another embodiment of a mitral valve assembly 190 including a valve 192 and a stent 194 (shown partially cut-away to expose a portion of the valve). Tension members, shown generally at 196, can be connected between leaflets 198, 200 of the valve 192 and the stent itself. Only two leaflets are shown, but additional tension members can be used for a third leaflet in a tricuspid valve. In the illustrated embodiment, the tension members 196 can include groups 202, 204 of three tension members each. The three tension members 196 of group 202 can be attached, at one end, to leaflet 198 at spaced intervals and converge to attach at an opposite end to a bottom 206 of the stent 194. Group 204 can be similarly connected between leaflet 200 and the bottom 206 of the stent 194. The tension members 196 can be made of any suitable biocompatible material, such as traditional suture material, GORE-TEX®, or an elastomeric material, such as polyurethane. The tension members can prevent the leaflets 198, 200 from everting so as to minimize or prevent regurgitation through the valve assembly. As such, the tension members de-stress the moveable portions of the leaflets when the leaflets close during systole without the need to connect the tension members to the inner or outer wall of the heart.

Although groups of three tension members are illustrated, other connection schemes can be used. For example, each group can include any desired number of tension members (e.g., 1, 2, 3, . . . etc.). Additionally, the tension members can connect to any portion of the stent 194 and at spaced intervals, if desired. Likewise, the tension members can connect to the leaflets at a point of convergence, rather than at spaced intervals. Further, the tension members can be used on bicuspid or tricuspid valves. Still further, it should be understood that tension members extending between the stent and the leaflets can be used on any of the embodiments disclosed herein.

Figures 12, 13, 14, 17:
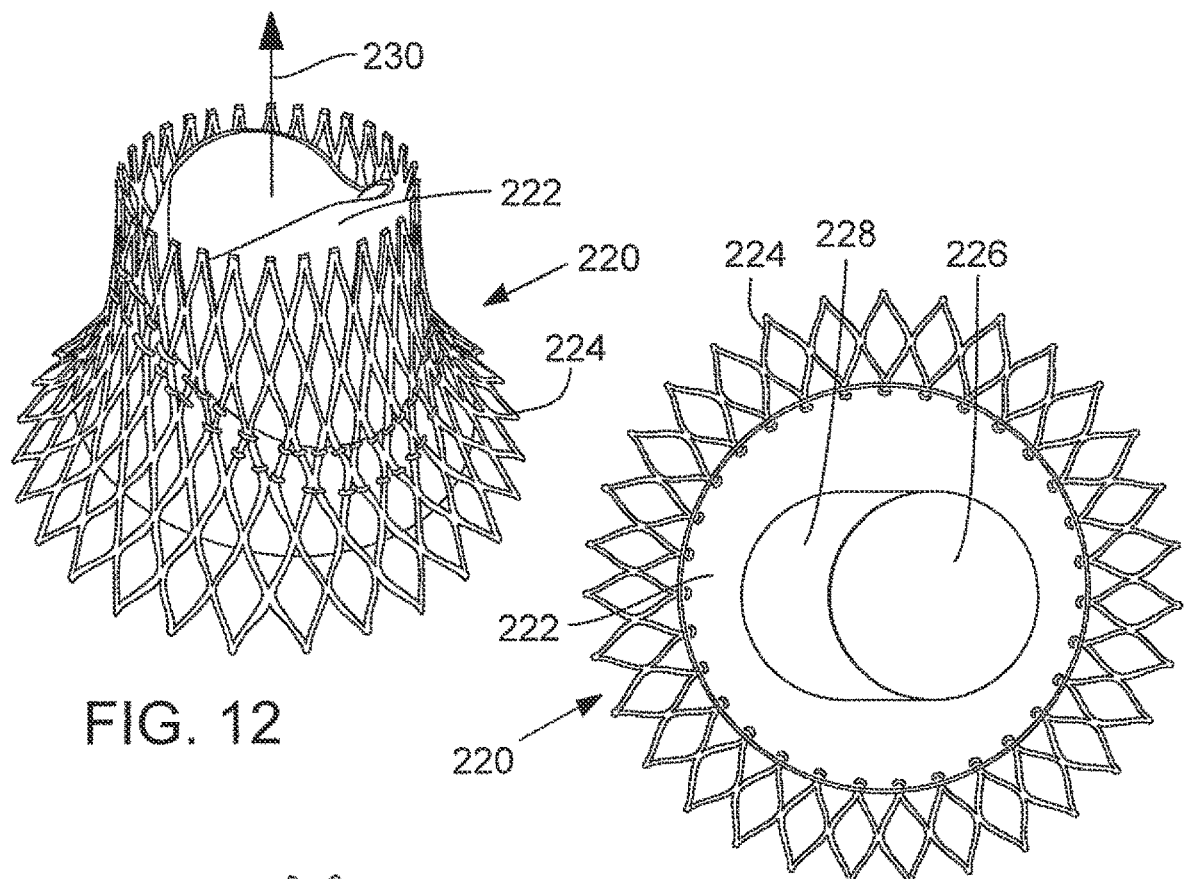
FIG. 12 is a perspective view of a prosthetic valve assembly having a bicuspid valve, according to another embodiment.
FIG. 13 is a top view of the prosthetic valve assembly of FIG. 12 with the bicuspid valve in a closed or at-rest position.
FIG. 14 is a top view of the prosthetic valve assembly of FIG. 12 with the bicuspid valve in an open position.
FIG. 17 is a cross-sectional view of a prosthetic valve assembly having a non-uniform cross-sectional shape.

FIGS. 12-14 show another embodiment of a mitral valve assembly 220 including a bicuspid valve 222 mounted within a stent 224. The bicuspid valve 222 can include two unequally-sized leaflets, 226, 228. FIG. 12 shows a perspective view of the mitral valve assembly 220 with the bicuspid valve 222 in an open position with blood flow shown by directional arrow 230. FIG. 14 shows a top view of the mitral valve assembly 220 with the valve 222 in the open position. FIG. 13 shows a top view of the mitral valve assembly 220 with the bicuspid valve 222 in a closed position. The leaflet 226 is shown as a larger leaflet than leaflet 228 with the leaflets overlapping in a closed or at-rest position. The overlapping configuration can provide sufficient closure of the valve to prevent central or coaptation leakage and can enhance valve durability by eliminating or minimizing impacts on the leaflet touching or coaptation. The bicuspid valve 222 can be used with any of the stent configurations described herein.

Figure 15:
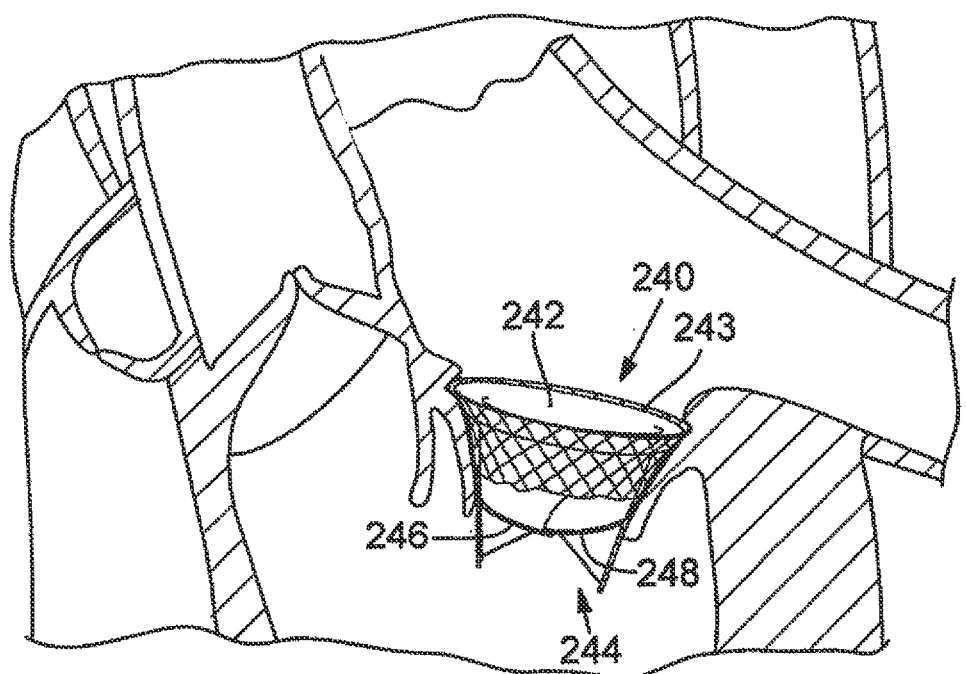
FIG. 15 is a perspective view of a prosthetic valve assembly having tensioning members coupled to a bicuspid valve in a closed position, according to another embodiment.
Figure 16:
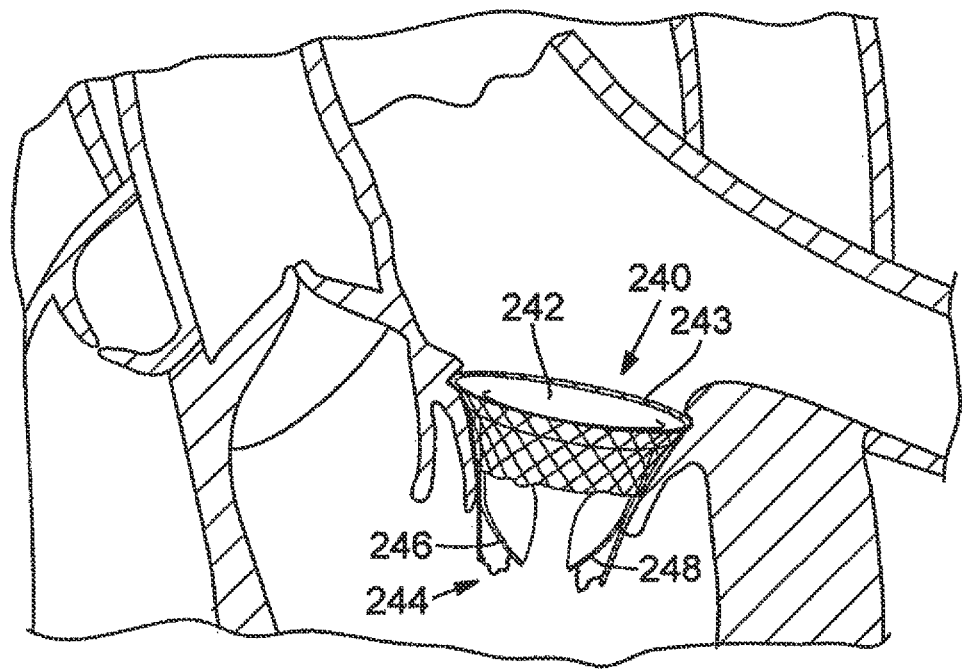
FIG. 16 is a perspective view of the prosthetic valve assembly of FIG. 15 with the bicuspid valve in an open position.

FIGS. 15 and 16 show another embodiment of a mitral valve assembly 240 including a bicuspid valve 242 mounted within a stent 243. Tension members, shown generally at 244, can be connected between leaflets 246, 248 of the valve and the stent itself. Leaflet 246 is shown as a larger leaflet that overlaps leaflet 248. FIG. 15 shows the mitral valve assembly 240 in a closed position with the tension members 244 at full extension. FIG. 16 shows the bicuspid valve 242 in the open position with the tension members 244 in a relaxed or slack state. Although the tension members 244 are shown attached at the same relative vertical position or height on the stent 243, the tension members 244 can be attached asymmetrically relative to each other. In other words, the tension members 244 can be attached at different heights along the length of the stent. Additionally, the tension members 244 can differ in length in order to achieve the asymmetrical coupling between the leaflets 246, 248 and the stent 243. The tensioning members 244 can be used on any of the mitral valve assembly embodiments described herein.

FIG. 17 shows a top view of a mitral valve assembly 260 having a non-uniform cross-sectional shape. The mitral valve assembly 260 can have a shape configured to conform to the natural opening of the native mitral valve. For example, the mitral valve assembly 260 can have a substantially "D" shape, with a substantially straight portion 262 and a substantially curved portion 264. When implanted, the substantially straight portion 262 can extend along the anterior side of the native mitral valve and the substantially curved portion 264 of the stent can extend along the posterior side of the native mitral valve. Other shapes may also be used.

Having illustrated and described the principles of the illustrated embodiments, it will be apparent to those skilled in the art that the embodiments can be modified in arrangement and detail without departing from such principles.

Although the transapical procedure shown in FIGS. 8A-8D illustrates positioning and deployment of mitral valve assembly 20, other embodiments of the mitral valve assembly disclosed herein can be implanted using the same procedure, such as the mitral valve assembly 100 of FIG. 6, or a mitral valve assembly using the stent of FIG. 7.

Further, although the mitral valve assembly 20 is shown generally circular in cross section, as noted above, it can have a D-shape, an oval shape or any other shape suitable for fitting the contours of the native mitral valve. Furthermore, although the mitral valve assembly is shown as having a flared upper end, other embodiments are contemplated, such as, for example, wherein the stent is flared at both ends or has a substantially cylindrical shape. Furthermore, the stent may be coated to reduce the likelihood of thrombi formation and/or to encourage tissue ingrowth using coatings known in the art. Still further, it is contemplated that the stent may be replaced with an alternative structure, such as an expandable tubular structure, which is suitable for anchoring the prosthetic valve member in the heart.

Still further, although a transapical procedure is described in detail in FIGS. 8A-8D, other procedures can be used in conjunction with the above-described embodiments. For example, U. S. Patent Publication 2004/0181238, to Zarbatany et al., entitled "Mitral Valve Repair System and Method for Use", which is hereby incorporated by reference, discloses a percutaneous delivery approach. A guidewire capable of traversing the circulatory system and entering the heart of the patient can be introduced into the patient through an endoluminal entry point, such as the femoral vein or the right jugular vein. The guidewire can then be directed into the right atrium where it traverses the right atrium and punctures the atrial septum using a trans-septal needle. The guidewire can then be advanced through the atrial septum, through the left atrium and through the mitral valve. Once the guidewire is properly positioned, a guide catheter can be attached to the guidewire and advanced proximate the native mitral valve. A delivery catheter for delivery of the prosthetic mitral valve can then be advanced through the guide catheter to deploy the prosthetic valve within the native mitral valve. Various delivery catheters can be used, such as those described in Zarbatany, as well as those described U.S. Patent Publication 2007/0088431, to Bourang et al., entitled "Heart Valve Delivery System With Valve Catheter" and U.S. Patent Publication U.S. 2007/0005131, to Taylor, entitled "Heart Valve Delivery System", both of which are hereby incorporated by reference.

In view of the many possible embodiments, it will be recognized that the illustrated embodiments include only examples of the invention and should not be taken as a limitation on the scope of the invention. Rather, the invention is defined by the following claims. We therefore claim as the invention all such embodiments that come within the scope of these claims.

We claim:

1. A prosthetic heart valve assembly for replacing a native mitral valve, the prosthetic heart valve assembly comprising:
    a self-expandable stent having a flared upper portion, a lower portion, and an intermediate portion extending from the upper portion to the lower portion, wherein the stent tapers from the upper portion toward the lower portion;
    a valve portion positioned within a passageway in the stent, wherein the valve portion comprises a plurality of leaflets made from bovine pericardium, wherein the valve portion permits flow of blood through the passageway in one direction for replacing the function of the native mitral valve;
    upwardly bent hooks extending from an outer surface of the stent, wherein each of the hooks extends toward the flared upper portion for engaging native leaflet tissue; and
    an elongate anchoring member extending from the lower portion of the stent, wherein the elongate anchoring member is adapted to be secured to a ventricle wall via a prong portion;
    wherein the prosthetic heart valve assembly is adapted to be retained in a radially compressed state within a delivery catheter and adapted to radially self-expand to an expanded state when deployed from the delivery catheter; and
    wherein, when deployed within the native mitral valve, the flared upper portion contacts a supra-annular surface of the native mitral valve for preventing downward migration of the prosthetic heart valve assembly toward a ventricle and the upwardly bent hooks and the elongate anchoring member prevent upward migration of the prosthetic heart valve assembly toward an atrium.

2. The prosthetic heart valve assembly of claim 1, wherein the self-expandable stent has a D-shape for conforming to the annulus of the native mitral valve.

3. The prosthetic heart valve assembly of claim 1, wherein the self-expandable stent is made from a shape memory material.

4. The prosthetic heart valve assembly of claim 1, wherein the prosthetic heart valve assembly is sized for advancement through a femoral vein when in a compressed state.

5. The prosthetic heart valve assembly of claim 1, wherein the prosthetic heart valve assembly is sized for advancement through a jugular vein when in the compressed state.

6. The prosthetic heart valve assembly of claim 1, wherein the prong portion comprises one or more prongs configured to penetrate the ventricle wall when the prosthetic heart valve assembly is implanted in the native mitral valve.

7. A prosthetic heart valve assembly for replacing a native heart valve, the prosthetic heart valve assembly comprising:
    a self-expandable stent having a flared upper portion, a lower portion, and an intermediate portion extending from the upper portion to the lower portion, wherein the stent tapers from the upper portion toward the lower portion;
    a valve portion positioned within a passageway in the stent, wherein the valve portion comprises a plurality of leaflets, wherein the valve portion permits flow of blood through the passageway in one direction for replacing the function of the native heart valve;
    upwardly bent hooks extending from an outer surface of the stent, wherein each of the hooks extends toward the flared upper portion for engaging native leaflet tissue; and
    an elongate anchoring member extending from the lower portion, wherein the elongate anchoring member is adapted to be secured to a septum of a ventricle via a prong portion at a location below the leaflets of the valve portion;
    wherein the prosthetic heart valve assembly is configured to be retained in a radially compressed state within a delivery catheter and adapted to radially self-expand to an expanded state when deployed from the delivery catheter; and
    wherein, when deployed within the native heart valve, the flared upper portion contacts a supra-annular surface of the native heart valve for preventing downward migration of the prosthetic heart valve assembly toward the ventricle and the upwardly bent hooks and the elongate anchoring member prevent upward migration of the prosthetic heart valve assembly toward an atrium.

8. The prosthetic heart valve assembly of claim 7, wherein the stent has a truncated conical shape.

9. The prosthetic heart valve assembly of claim 7, wherein the stent has a length between 15-50 mm.

10. The prosthetic heart valve assembly of claim 7, wherein the prosthetic heart valve assembly is configured to be advanced through a jugular vein and into a heart with the delivery catheter.

11. The prosthetic heart valve assembly of claim 7, wherein the prong portion comprises a plurality of prongs configured to penetrate the septum when the prosthetic heart valve assembly is implanted in the native heart valve between the atrium and the ventricle.

12. The prosthetic heart valve assembly of claim 7, wherein the prong portion comprises a pair of prongs.

13. The prosthetic heart valve assembly of claim 12, wherein the pair of prongs form a branched double hook.

14. The prosthetic heart valve assembly of claim 12, wherein the pair of prongs are configured to be transitioned from a radially compressed state to a deployed state after positioning of the prosthetic heart valve assembly in the native heart valve.

15. A prosthetic heart valve assembly for replacing a native heart valve, the prosthetic heart valve assembly comprising:
   a self-expandable stent having a flared upper portion, a lower portion and an intermediate portion extending from the upper portion toward the lower portion;
   a valve portion comprising a plurality of leaflets positioned within a passageway in the stent, wherein the valve portion permits flow of blood through the passageway in one direction for replacing the function of the native heart valve;
   one or more first anchoring members extending from an outer surface of the stent, wherein the one or more first anchoring members are adapted to engage native leaflet tissue; and
   one or more second anchoring members extending from the lower portion of the stent, wherein the one or more second anchoring members are adapted to engage a ventricle wall;
   wherein the prosthetic heart valve assembly is configured to be retained in a radially compressed state within a delivery catheter and radially self-expand to a radially expanded state when deployed from the delivery catheter; and
   wherein, when deployed within the native heart valve, the flared upper portion contacts a supra-annular surface of the native heart valve for preventing downward migration of the prosthetic heart valve assembly toward a ventricle and the one or more first anchoring members and the one or more second anchoring members prevent upward migration of the prosthetic heart valve assembly toward an atrium.

16. The prosthetic heart valve assembly of claim 15, wherein the flared upper portion has a D-shape configuration.

17. The prosthetic heart valve assembly of claim 15, wherein the one or more first anchoring members comprise one or more upwardly bent hooks, wherein a tip of each of the one or more hooks is oriented toward the flared upper portion.

18. The prosthetic heart valve assembly of claim 15, wherein the leaflets have outflow ends that are located at an outflow end of the stent.

19. The prosthetic heart valve assembly of claim 15, wherein the stent is shaped to fit the contours of native leaflets of the native heart valve.

20. The prosthetic heart valve assembly of claim 15, wherein each of the one or more second anchoring members comprises a plurality of prongs formed from a shape memory material that are adapted to be expandable from a compressed state to a deployed state in which the prongs engage the ventricle wall at a location below the leaflets of the valve portion.

21. The prosthetic heart valve assembly of claim 20, wherein the ventricle wall is a septum of the ventricle.

* * * * *